United States Patent
Louis et al.

(10) Patent No.: US 9,868,825 B2
(45) Date of Patent: Jan. 16, 2018

(54) POLYARYLENE ETHER SULFONE (PAES) POLYMERS

(71) Applicant: SOLVAY SPECIALTY POLYMERS USA, LLC, Alpharetta, GA (US)

(72) Inventors: Chantal Louis, Alpharetta, GA (US); Mohammad Jamal El-Hibri, Atlanta, GA (US); David B. Thomas, Atlanta, GA (US); Hemantkumar Patel, Alpharetta, GA (US)

(73) Assignee: SOLVAY SPECIALTY POLYMERS USA, LLC, Alpharetta, GA (US)

( * ) Notice: Subject to any disclaimer, the term of this patent is extended or adjusted under 35 U.S.C. 154(b) by 0 days.

(21) Appl. No.: 14/889,635

(22) PCT Filed: Apr. 30, 2014

(86) PCT No.: PCT/EP2014/058799
§ 371 (c)(1),
(2) Date: Nov. 6, 2015

(87) PCT Pub. No.: WO2014/180724
PCT Pub. Date: Nov. 13, 2014

(65) Prior Publication Data
US 2016/0090450 A1    Mar. 31, 2016

Related U.S. Application Data

(60) Provisional application No. 61/820,855, filed on May 8, 2013.

(30) Foreign Application Priority Data

Jul. 26, 2013 (EP) ..................................... 13178120

(51) Int. Cl.
*C08G 64/00* (2006.01)
*C08G 75/23* (2006.01)
(Continued)

(52) U.S. Cl.
CPC ............. *C08G 75/23* (2013.01); *B05D 1/12* (2013.01); *B29C 43/003* (2013.01);
(Continued)

(58) Field of Classification Search
CPC ...... C08G 2261/516; C08G 2261/1452; C08G 2261/722; C08G 18/0828; H01B 1/122; H01M 8/1025; H01M 8/1027
See application file for complete search history.

(56) References Cited

U.S. PATENT DOCUMENTS

5,204,442 A * 4/1993 Nye ........................ C08G 65/40
528/125
6,069,223 A * 5/2000 Liggat ................ C08G 65/4012
528/171

(Continued)

FOREIGN PATENT DOCUMENTS

EP    383600 A2    8/1990
EP    401603 A1    12/1990
(Continued)

OTHER PUBLICATIONS

Mao M. et al., "Synthesis and characterization of poly(aryl ether sulfone) copolymers containing terphenyl groups in the backbone", Polymer, 2007, vol. 48(21), p. 6241-6245—Elsevier Ltd., XP022278391, ISSN: 0032-3861, DOI: 101016/J.POLYMER.2007.08.036.

Robeson L.M. et al., "Synthesis and Dynamic Mechanical Characteristics of Poly(Ary Ethers)", Applied Polymer Symposium, 1975, n° 26, p. 373-385—John Wiley & Sons, Inc.

Staniland, P. A., "Synthesis and properties of novel polyether ketones and polyether sulfones", Bulletin des 5ocietes Chimiques Beiges, 1989, vol. 98(9-10), p. 667-76.

Salunke A.K., "Synthesis and characterization of poly(arylene ether)s derived from 4,4'-bishydroxybiphenyl and 4,4'-bishydroxyterphenyl", Journal of Polymer Science, Part A: Polymer Chemistry, 2001, Volume Date 2002, vol. 40(1), p. 55-69—John Wiley & Sons, Inc.

(Continued)

*Primary Examiner* — Shane Fang
(74) *Attorney, Agent, or Firm* — Jarrod N. Raphael; Dwight M. Benner II

(57) ABSTRACT

A poly(arylether sulfone) polymer [(t-PAES) polymer, herein after], wherein more than 70% moles of the recurring units are recurring units ($R_t$) of formula (St): -E-$Ar_1$—$SO_2$-[$Ar_2$-(T-$Ar_3$)$_n$—$SO_2$]m-$Ar_4$— (formula $S_t$) wherein: n and m, equal to or different from each other, are independently zero or an integer of 1 to 5, each of $Ar_1$, $Ar_2$, $Ar_3$ and $Ar_4$ equal to or different from each other and at each occurrence, is an aromatic moiety, T is a bond or a divalent group optionally comprising one or more than one heteroatom; -E is of formula ($E_t$), wherein each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; j' is zero or is an integer from 1 to 4, and said (t-PAES) polymer having a number average molecular weight ($M_n$) ranging from 41 000 to 90 000.

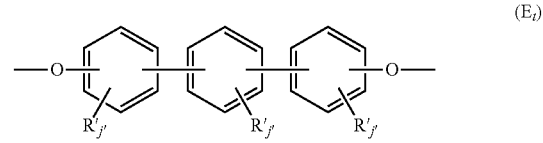

($E_t$)

21 Claims, No Drawings

(51) Int. Cl.
    *B05D 1/12*     (2006.01)
    *B29C 43/00*     (2006.01)
    *B29C 45/00*     (2006.01)
    *B29C 47/00*     (2006.01)
    *B29C 67/00*     (2017.01)
    *G01N 30/02*     (2006.01)
    *B33Y 10/00*     (2015.01)
    *B33Y 70/00*     (2015.01)
    *B29K 81/00*     (2006.01)

(52) U.S. Cl.
    CPC ...... *B29C 45/0001* (2013.01); *B29C 47/0004* (2013.01); *B29C 67/0055* (2013.01); *G01N 30/02* (2013.01); *B29K 2081/06* (2013.01); *B33Y 10/00* (2014.12); *B33Y 70/00* (2014.12)

(56) References Cited

U.S. PATENT DOCUMENTS

2006/0030683 A1    2/2006    Moore et al.
2009/0124767 A1    5/2009    El-Hibri

FOREIGN PATENT DOCUMENTS

| EP | 407714 A2 | 1/1991 |
|---|---|---|
| GB | 2289685 A | 11/1995 |
| JP | 37072301 A | 3/1995 |
| WO | 9531502 A1 | 11/1995 |

OTHER PUBLICATIONS

Zhang B. et al., "Synthesis of cyclohexylene ring containing semi-crystalline poly(arylene ether sulfones)(PAES)", Polymer Preprints (American Chemical Society, Division of Polymer Chemistry), 2010, vol. 51(2), p. 217-218.

Cureton L.T. et al., "Synthesis and properties of bisphenol A-terphenol poly(arylene ether sulfone)-polydimethylsiloxane segmented block copolymers", European Polymer Journal, 2011, vol. 47(12), p. 2303-2310—Elsevier Ltd.

Zhang B. et al., "New polyarylene ether sulfones based on 4,4'-trans-1,4-cyclohexanediylbismethylene bisphenol", Polymer, 2013, vol. 54(19), p. 4493-4500—XP002718895.

Kwiatkowski, G. T. et al., "Aromatic biphenylene polymers: synthesis via nickel coupling of aryl dichlorides", Makromolekulare Chemie, Macromolecular Symposia, 1992, 54/55(Int. Symp. New Polym. React. React. Mech., 1991), p. 199-224—Hüthig & Wepf Verlag, Basel.

Staniland, P. A., "Synthesis and environmental resistance of thermoplastic matrix and adhesive resins for composites", Polymer Preprints (American Chemical Society, Division of Polymer Chemistry), 1992, vol. 33(1), p. 104-5.

\* cited by examiner

POLYARYLENE ETHER SULFONE (PAES) POLYMERS

This application claims priority to U.S. provisional application No. 61/820,855 filed on 8 May 2014 and to European application No. 13178120.5 filed on 26 Jul. 2013, the whole content of each of these applications being incorporated herein by reference for all purposes.

FIELD OF INVENTION

The present invention relates to polyarylene ether sulfone (PAES) polymers comprising moieties derived from incorporation of 4,4"-terphenyl-p-diol, to a process for the manufacture of said polyarylene ether sulfone (PAES) polymers.

BACKGROUND OF THE INVENTION

The selection of polymeric material in more demanding, corrosive, harsh chemical, high-pressure and high-temperature (HP/HT) environments, such as notably in oil and gas downhole applications, in particular in deep see oil wells, is of ultimate importance as it implies that said polymeric materials need to possess some critical properties in order to resist the extreme conditions associated with said environments.

It should be mentioned that in these extreme conditions the polymeric materials are exposed in a prolonged fashion to high pressure, e.g. pressures higher than 30,000 psi, high temperatures, e.g. temperatures up to 260° C., and to harsh chemicals including acids, bases, superheated water/steam, and of course a wide variety of aliphatic and aromatic organics. For example, enhanced oil recovery techniques involve injecting of fluids such as notably water, steam, hydrogen sulfide ($H_2S$) or supercritical carbon dioxide ($sCO_2$) into the well. In particular, $sCO_2$ having a solvating effect similar to n-heptane, can cause swelling of materials in for instance seals, which affect consequently their performance. Polymeric materials having too low glass transition temperatures (Tg) relative to the high temperature in HP/HT applications will suffer from being weak and susceptible to high creep in these HP/HT applications. This creep can cause the seal material made of said polymeric material to no longer effectively seal after prolonged exposure at temperature which are 20 or more ° C. above their Tg.

Thus, properties such as maintaining mechanical rigidity and integrity (e.g. tensile strength and modulus, hardness and impact toughness) at high pressure and temperatures of at least 250° C., good chemical resistance, in particular when exposed to $CO_2$, $H_2S$, amines and other chemicals at said high pressure and temperature, swelling and shrinking by gas and by liquid absorption, decompression resistance in high pressure oil/gas systems, gas and liquid diffusion and long term thermal stability need to be considered in the selection of appropriate polymeric materials for HP/HT applications.

Thus said polymeric materials need at least to possess a high glass transition temperature.

The utility of aromatic sulfone ether polymers in applications combining high thermal and chemical exposure has been limited due to the fact that said aromatic sulfone ether polymers are large amorphous materials and are therefore very limited in their chemical resistance. Semi-crystalline aromatic sulfone ether polymers are extremely rare.

Staniland reports notably in Table 1 of Polymer Preprints, American Chemical Society, Division of Polymer Chemistry, 1992, 33(1), pages 404-405, some crystalline polyethersulphone polymers having high transition glass temperatures (Tg) of above 200° C. and having melting temperatures of below 400° C. (e.g. Structures 1-4 and 7). The author is in particular referring to the polyethersulphone polymer of structure 4 described therein (i.e. —OØØØOØSO$_2$Ø-, being understood that ≡ is Ph or a phenyl group) derived from 4,4' dichlorodiphenyl sulfone (DCDPS) and dihydroxyterphenylene, which has a Tg of 251° C. and a Tm of 359° C. Said polyethersulphone polymer of structure 4 was already earlier disclosed by the same author in Bulletin des Societes Chimiques Belges, 1989, 98 (9-10), pages 667-676. FIG. 6 of this paper shows notably a DSC (differential scanning calorimetry) scan of the polyethersulphone polymer of structure 4. Said polyethersulphone polymer has a 41% crystallinity when the crystallinity was measured on the powder obtained after isolation from the polymerization reactor. However, a crystallinity level of a molded film of 38% could be regained when said molded film was annealed at 325° C.

Said polyethersulphone polymer of structure 4 is also disclosed in EP 0 383 600 A2, in particular, examples 1 and 2 describe the reaction of dichlorodiphenylsulfone (DCDPS, e.g. example 1) or difluorodiphenylsulfone (DFDPS, e.g. example 2) with 4,4"-terphenyl-p-diol (e.g. HO-Ph-Ph-Ph-OH, also called 4,4"-dihydroxyterphenylene). Said aromatic polymers described in example 1, respectively example 2 have a high transition glass temperature (Tg) of 241° C., respectively 251° C., a Tm melting point of 385° C., respectively 389° C., a very high crystallinity of 44%, respectively 41%-44% and a reduced viscosity (RV) measured at 25° C. on a solution of 1.0 g of polymer in 100 cm$^3$ $H_2SO_4$ of 0.27 (dL/g), respectively 1.40 (dL/g). As will be mentioned more in detail below, this example yielded a polymer with a M$_n$ of about 13,000-14,000 for polyethersulphone polymer of structure 4 when measured by a GPC method as described below. It should be mentioned that the crystallinity, as described in EP 0 383 600 A2 refers to a crystallinity that has been measured on the powder obtained after isolation from the polymerization reactor.

GB 2 289 685 A also discloses said polyethersulphone polymer of structure 4. In particular, example 12 describes the reaction of 4,4"-dihydroxyterphenylene with DFDPS thereby forming thus a polysulfone polymer containing repeat units of the formula —O-Ph-Ph-Ph-O-Ph-SO2-Ph-. The polymer obtained in said example 12 has an inherent viscosity (IV), measured at 25° C. on a solution of 0.1 g of polymer in 100 ml 98% $H_2SO_4$, of 0.40 (dL/g). As will be mentioned more in detail below, this example yielded a polymer with a M$_n$ of about 40,117 for polyethersulphone polymer of structure 4 when measured by a GPC method as described below.

It is known that thermosets due to their three dimensional network of bonds (i.e. cross-linking) are suitable to be used in high temperature applications up to the decomposition temperature. However, one of the drawbacks is that they are more brittle.

In view of all the above, there is still a current shortfall in the art for polyarylene ether sulfone (PAES) polymers comprising recurring units derived from the 4,4"-terphenyl-p-diol, which are readily accessible through a more efficient and controlled synthetic route and wherein said (PAES) polymers have an excellent balance of (1) stiffness and ductility, (2) crystallizability and chemical resistance (3) high thermal resistance (e.g. Tg>230° C.), long term thermal stability and adequate processability (e.g. Tm<420° C.), and thus can provide improved performance relative to current polymeric materials for HP/HT applications.

DETAILED DESCRIPTION OF THE PRESENT INVENTION

The Applicant has now found that it is possible to advantageously manufacture polyarylene ether sulfone (PAES) polymers comprising moieties derived from incorporation of 4,4"-terphenyl-p-diol wherein said (PAES) polymers have controlled high molecular weights and are advantageously fulfilling all the above mentioned needs, including maintaining mechanical rigidity and integrity, maintaining an adequate crystallinity and having good chemical resistance at high pressure and temperature.

It is thus an object of the present invention, a poly (arylether sulfone) polymer [(t-PAES) polymer, herein after], wherein more than 70% moles of the recurring units are recurring units ($R_t$) of formula ($S_t$):

$$\text{-E-Ar}^1\text{—SO}_2\text{—[Ar}^2\text{-(T-Ar}^3)_n\text{—SO}_2]_m\text{—Ar}^4\text{—} \quad \text{(formula } S_t\text{)}$$

wherein:
n and m, equal to or different from each other, are independently zero or an integer of 1 to 5,
each of $Ar^1$, $Ar^2$, $Ar^3$ and $Ar^4$ equal to or different from each other and at each occurrence, is an aromatic moiety,
T is a bond or a divalent group optionally comprising one or more than one heteroatom; preferably T is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

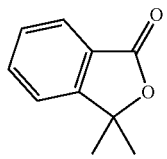

E is of formula ($E_t$):

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 1 to 4, and
said (t-PAES) polymer having a number average molecular weight ($M_n$) ranging from 41 000 to 90 000.

The (t-PAES) polymer of the present invention characterized by having a specific high number average molecular weight ($M_n$) ranging from 41 000 to 90 000 advantageously possesses a unique combination of properties like, notably, high Tg, high stiffness and strength, and interesting toughness, and good crystallizability and good chemical resistance.

The (t-PAES) Polymer

The aromatic moiety in each of $Ar^1$, $Ar^2$, $Ar^3$ and $Ar^4$ equal to or different from each other and at each occurrence is preferably complying with following formulae:

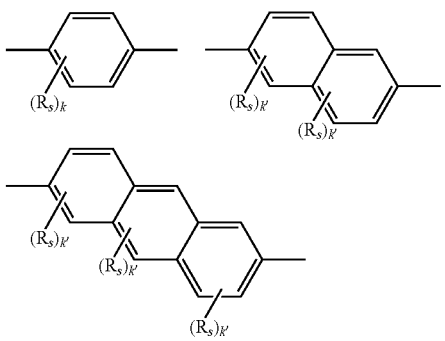

wherein:
each $R_s$ is independently selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and
k is zero or an integer of 1 to 4; k' is zero or an integer of 1 to 3.

In recurring unit ($R_t$), the respective phenylene moieties may independently have 1,2-, 1,4- or 1,3-linkages to the other moieties different from R or R' in the recurring unit. Preferably, said phenylene moieties have 1,3- or 1,4-linkages, more preferably they have 1,4-linkage.

Still, in recurring units ($R_t$), j', k' and k are at each occurrence zero, that is to say that the phenylene moieties have no other substituents than those enabling linkage in the main chain of the polymer.

Preferred recurring units ($R_t$) are selected from the group consisting of those of formula ($S_t$-1) to ($S_t$-4) herein below:

($S_t$1)

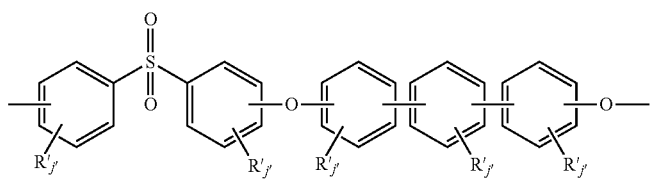

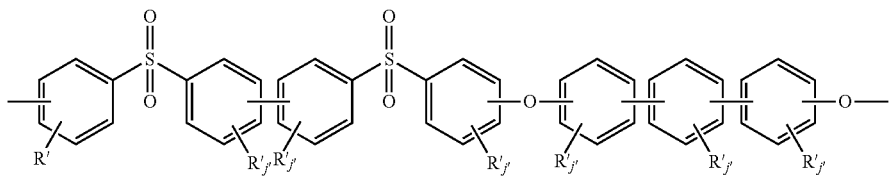

(S_r-2)

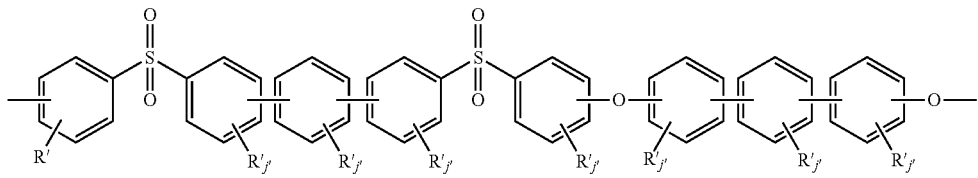

(S_r-3)

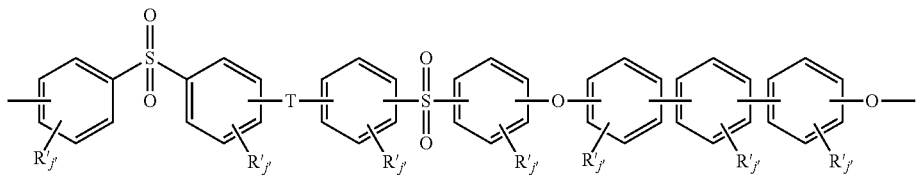

(S_r-4)

wherein
  each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
  j' is zero or is an integer from 1 to 4,
  T is a bond or a divalent group optionally comprising one or more than one heteroatom; preferably T is selected from the group consisting of a bond, —CH₂—, —C(O)—, —C(CH₃)₂—, —C(CF₃)₂—, —C(=CCl₂)—, —C(CH₃)(CH₂CH₂COOH)—, and a group of formula:

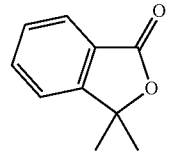

The above recurring units of preferred embodiments (R_r-1) to (R_r-4) can be each present alone or in admixture.

More preferred recurring units (R_r) are selected from the group consisting of those of formula (S_r-1) to (S_r-3) herein below:

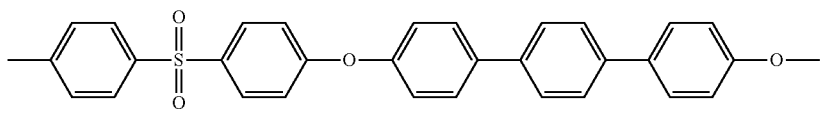

(S'_r-1)

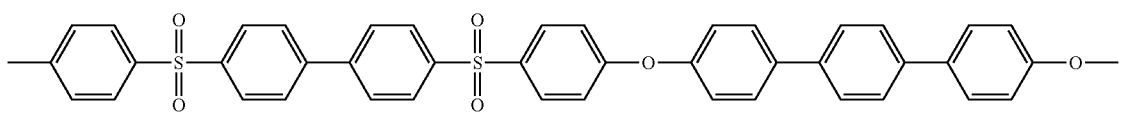

(S'_r-2)

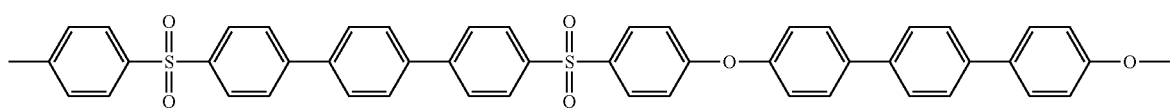

(S'_r-3)

Most preferred recurring unit ($R_t$) is of formula ($S'_t$-1), as shown above. According to certain embodiments, the (t-PAES) polymer, as detailed above, comprises in addition to recurring units ($R_t$), as detailed above, recurring units ($R_a$) of formula ($K_a$):

-E-Ar$^5$—CO—[Ar$^6$-(T-Ar$^7$)$_n$—CO]$_m$—Ar$^8$— (formula $K_a$)

wherein:
n and m, equal to or different from each other, are independently zero or an integer of 1 to 5,
each of Ar$^5$, Ar$^6$, Ar$^7$ and Ar$^8$ equal to or different from each other and at each occurrence, is an aromatic moiety, T is a bond or a divalent group optionally comprising one or more than one heteroatom; preferably T is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

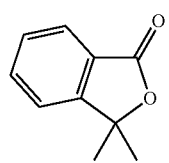

E is of formula ($E_r$), as detailed above.

Recurring units ($R_a$) can notably be selected from the group consisting of those of formulae ($K_a$-1) or ($K_a$-2) herein below:

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 1 to 4.

More preferred recurring units ($R_a$) are selected from the group consisting of those of formula ($K'_a$-1) or ($K'_a$-2) herein below:

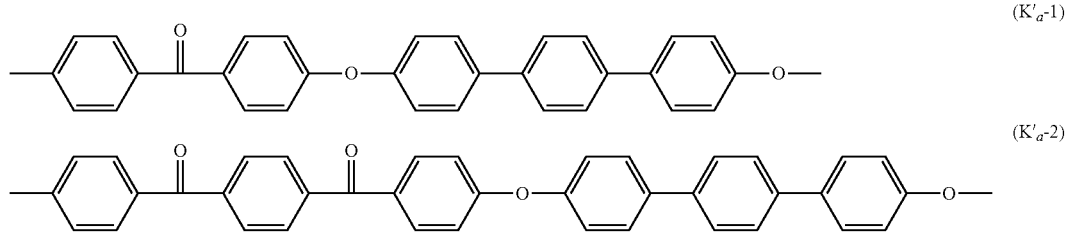

($K'_a$-1)

($K'_a$-2)

According to certain embodiments, the (t-PAES) polymer, as detailed above, comprises in addition to recurring units ($R_t$), as detailed above, recurring units ($R_b$) comprising a Ar—SO$_2$—Ar' group, with Ar and Ar', equal to or different from each other, being aromatic groups, said recurring units ($R_b$) generally complying with formulae (S1):

—Ar$^9$-(T'-Ar$^{10}$)$_n$—O—Ar$_{11}$—SO$_2$—[Ar$^{12}$-(T-Ar$^{13}$)$_n$—SO$_2$]$_m$—Ar$^{14}$—O— (S1):

wherein:
Ar$^9$, Ar$^{10}$, Ar$^{11}$, Ar$^{12}$, Ar$^{13}$ and Ar$^{14}$, equal to or different from each other and at each occurrence, are independently a aromatic mono- or polynuclear group;
T and T', equal to or different from each other and at each occurrence, is independently a bond or a divalent group optionally comprising one or more than one heteroatom; preferably T' is selected from the group consisting of a bond, —CH$_2$—, —C(O)—, —C(CH$_3$)$_2$—,

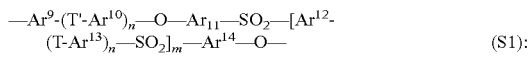

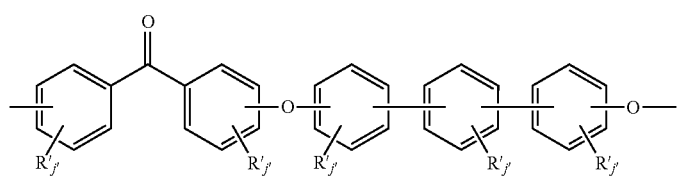

($K_a$-1)

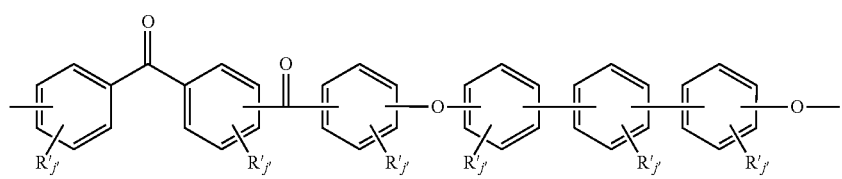

($K_a$-2)

—C(CF$_3$)$_2$—, —C(=CCl$_2$)—, —C(CH$_3$)(CH$_2$CH$_2$COOH)—, —SO$_2$—, and a group of formula:

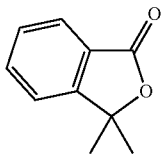

preferably T is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

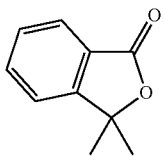

n and m, equal to or different from each other, are independently zero or an integer of 1 to 5;

Recurring units (R$_b$) can be notably selected from the group consisting of those of formulae (S1-A) to (S1-D) herein below:

than one heteroatom; preferably T' is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, —SO$_2$—, and a group of formula:

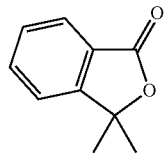

preferably T is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

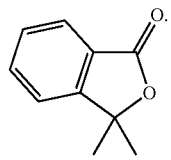

In recurring unit (R$_b$), the respective phenylene moieties may independently have 1,2-, 1,4- or 1,3-linkages to the other moieties different from R' in the recurring unit. Preferably, said phenylene moieties have 1,3- or 1,4-linkages,

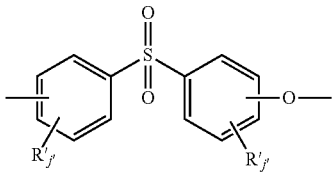 (S1-A)

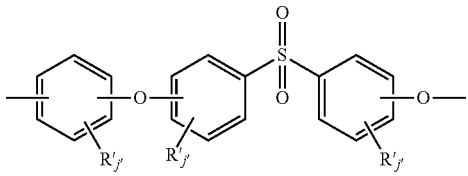 (S1-B)

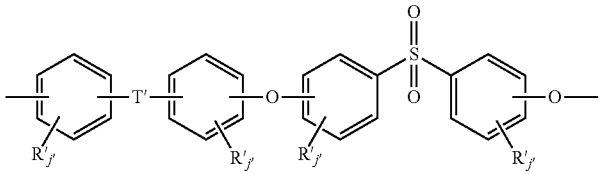 (S1-C)

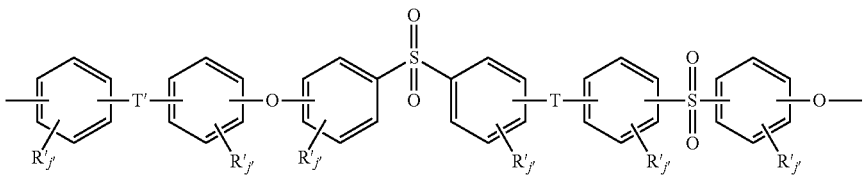 (S1-D)

wherein:
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 0 to 4;
T and T', equal to or different from each other are a bond or a divalent group optionally comprising one or more more preferably they have 1,4-linkage. Still, in recurring units (R$_b$), j' is at each occurrence zero, that is to say that the phenylene moieties have no other substituents than those enabling linkage in the main chain of the polymer.

According to certain embodiments, the (t-PAES) polymer, as detailed above, comprises in addition to recurring units (R$_t$), as detailed above, recurring units (R$_c$) comprising a Ar—C(O)—Ar' group, with Ar and Ar', equal to or different from each other, being aromatic groups, said recurring units (R$_c$) being generally selected from the group consisting of formulae (J-A) to (J-L), herein below:

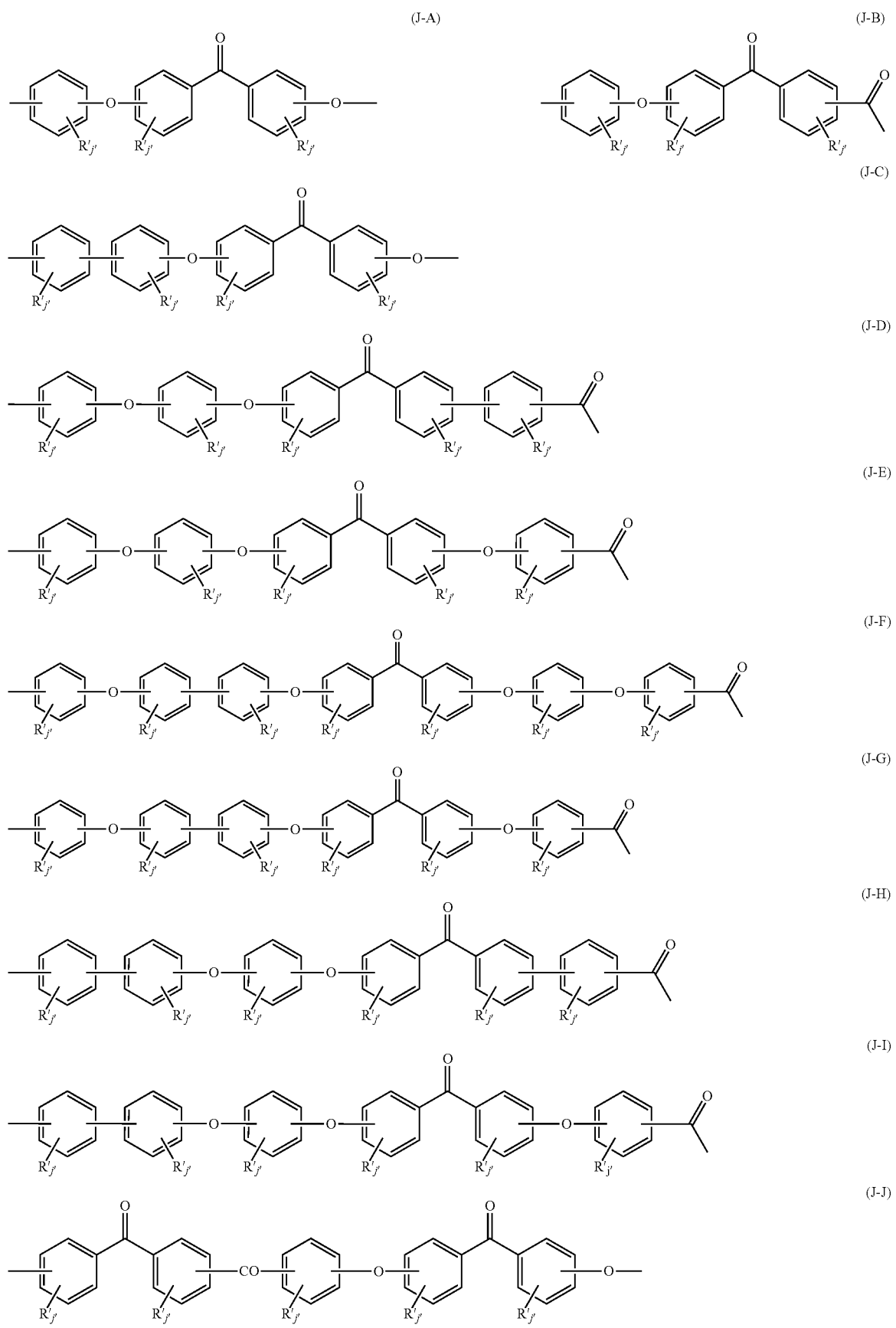

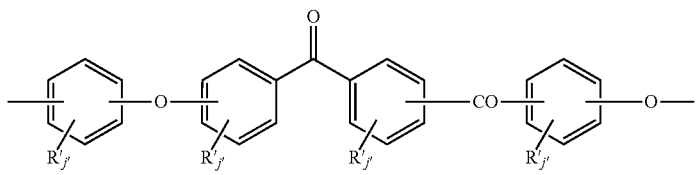

(J-K)

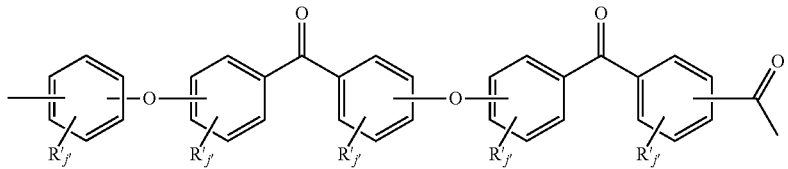

(J-L)

wherein:
- each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
- j' is zero or is an integer from 0 to 4.

In recurring unit ($R_c$), the respective phenylene moieties may independently have 1,2-, 1,4- or 1,3-linkages to the other moieties different from R' in the recurring unit. Preferably, said phenylene moieties have 1,3- or 1,4-linkages, more preferably they have 1,4-linkage.

Still, in recurring units ($R_c$), j' is at each occurrence zero, that is to say that the phenylene moieties have no other substituents than those enabling linkage in the main chain of the polymer.

As said, the (t-PAES) polymer comprises recurring units ($R_t$) of formula ($S_t$) as above detailed in an amount of more than 70% moles, preferably more than 75% moles, more preferably more than 85% moles, even more preferably more than 90% moles, most preferably more than 90% moles, the complement to 100% moles being generally recurring units ($R_a$), as above detailed, and/or recurring units ($R_b$), and/or recurring units ($R_c$), as above detailed.

Still more preferably, essentially all the recurring units of the (t-PAES) polymer are recurring units ($R_t$), chain defects, or very minor amounts of other units might be present, being understood that these latter do not substantially modify the properties of the (t-PAES) polymer. Most preferably, all the recurring units of the (t-PAES) polymer are recurring units ($R_t$). Excellent results were obtained when the (t-PAES) polymer was a polymer of which all the recurring units are recurring units ($R_t$), as above detailed.

To the aim of providing polymers particularly suitable for being used in HP/HT applications, in particular in oil and gas downhole operations, the (t-PAES) polymer of the invention has advantageously a number average weight ($M_n$) ranging from 41 000 to 90 000, preferably ranging from 41 000 to 85 000, preferably ranging from 43 000 to 85 000, and preferably ranging from 43 000 to 80 000.

Good results were obtained when the number average molecular weight ($M_n$) of the (t-PAES) polymer of the invention was ranging from 41 000 to 80 000.

In one embodiment of the present invention, the (t-PAES) polymer of the invention has advantageously a number average molecular weight ($M_n$) equal to or below 90 000, preferably equal to or below 85 000, preferably equal to or below 80 000, preferably equal to or below 75 000, preferably equal to or below 70 000, preferably equal to or below 65 000, preferably equal to or below 60 000, preferably equal to or below 55 000, preferably equal to or below 50 000.

The (t-PAES) polymer having such specific molecular weight ($M_n$) range have been found to possess an excellent ductility (i.e high tensile elongation), good thoughness while maintaining high Tg, and good crystallizability and good chemical resistance.

The number average molecular weight ($M_n$) is:

$$M_n = \frac{\sum M_i \cdot N_i}{\sum N_i}$$

wherein $M_i$ is the discrete value for the molecular weight of a polymer molecule, $N_i$ is the number of polymer molecules with molecular weight $M_i$, then the weight of all polymer molecules is $\Sigma M_i N_i$ and the total number of polymer molecules is $\Sigma N_i$.

$M_n$ can be suitably determined by gel-permeation chromatography (GPC) calibrated with polystyrene standards.

Other molecular parameters which can be notably determined by GPC are the weight average molecular weight ($M_w$):

$$M_w = \frac{\sum M_i^2 \cdot N_i}{\sum M_i \cdot N_i},$$

wherein $M_i$ is the discrete value for the molecular weight of a polymer molecule, $N_i$ is the number of polymer molecules with molecular weight then the weight of polymer molecules having a molecular weight $M_i$ is $M_i N_i$.

For the purpose of the present invention, the polydispersity index (PDI) is hereby expressed as the ratio of weight average molecular weight ($M_w$) to number average molecular weight ($M_n$).

The details of the GPC measurement are described in detail in the method description given in the experimental section.

For the determination of the number average molecular weight ($M_n$) by GPC, the (t-PAES) polymer is generally dissolved in a solvent suitable for GPC providing hereby a polymer solution.

A specimen of said polymer solution or a diluted specimen can then be injected into conventional GPC equipment.

The concentration of the (t-PAES) polymer in the polymer solution [polymer concentration, herein after] is between 1.0 to 10.0 mg/ml, preferably between 1.5 to 5.0 mg/ml, more preferably between 2.0 to 3.0 mg/ml. Good results were obtained with a concentration of the (t-PAES) polymer in the polymer solution of about 2.5 mg/ml.

Preferred solvents and solvent blends suitable to dissolve the (t-PAES) polymer of the present invention for determination of the $M_n$ values are for example 4-chlorophenol, 2-chlorophenol, meta-cresol. 4-chlorophenol is most preferred.

The dissolving of the (t-PAES) polymer of the present invention is advantageously carried out at a temperature from 100 to 250° C., preferably from 120 to 220° C. and more preferably from 170 to 200° C.

For the determination of the $M_n$ values by GPC, N-methyl-2-pyrrolidone (NMP) containing at least one salt is suitably used as eluent.

Suitable salts for use in NMP include lithium bromide and lithium chloride. Lithium bromide is most preferred.

The molar concentration of said salt present in NMP can vary from 0.05 mole salt per liter NMP to 0.2 mole salt per liter NMP. Good results were obtained when the molar concentration of said salt present in NMP is about 0.1 mole salt per liter NMP.

In a preferred embodiment, a specimen of said polymer solution, before injecting into the GPC equipment, is further diluted by the eluent thereby providing a diluted polymer solution [polymer solution (2), herein after].

In this preferred embodiment, the concentration of the (t-PAES) polymer in the polymer solution (2) [polymer concentration (2), herein after] is between 0.05 to 0.50 mg/ml, preferably between 0.10 to 0.25 mg/ml, more preferably between 0.20 to 0.25 mg/ml. Good results were obtained with a concentration of the (t-PAES) polymer in the polymer solution (2) of about 0.25 mg/ml.

The GPC measurements are in general carried out at a temperature from 20 to 50° C., preferably from 30 to 50° C., more preferably from 35 to 45° C. Good results were obtained when the temperature was about 40° C.

The GPC measurements are in general carried out at a pump flow rate from 0.3 to 0.9 ml/min, preferably from 0.5 to 0.7 ml/min. Good results were obtained when the flow rate was about 0.5 ml/min.

It is understood that the calibration with the polystyrene standards is carried out according to ordinary skills in the art. The details of said calibration with the polystyrene standards can be found in the experimental section below.

Another aspect of the present invention is related to the GPC measurement as described above.

The (t-PAES) polymer of the present invention has advantageously a polydispersity index (PDI) of more than 1.95, preferably more than 2.00, more preferably more than 2.05, and more preferably more than 2.10.

The (t-PAES) polymer of the present invention generally has a polydispersity index of less than 4.0, preferably of less than 3.8, more preferably of less than 3.5.

In addition, some other analytical methods can be used as an indirect method for the determination of molecular weight including notably viscosity measurements.

In one embodiment of the present invention, the (t-PAES) polymer of the present invention has a melt viscosity of advantageously at least 2.7 kPa·s, preferably at least 3.1 kPa·s, more preferably at least 3.2 kPa·s at 410° C. and a shear rate of 10 rad/sec, as measured using a parallel plates viscometer (e.g. TA ARES RDA3 model) in accordance with ASTM D4440. The (t-PAES) polymer of the present invention has a melt viscosity of advantageously of at most 46 kPa·s, preferably of at most 34 kPa·s, more preferably of at most 25 kPa·s at 410° C. and a shear rate of 10 rad/sec, as measured using a parallel plates viscometer (e.g. TA ARES RDA3 model) in accordance with ASTM D4440.

In another embodiment of the present invention, the (t-PAES) polymer of the present invention has a melt viscosity of advantageously at least 8.9 kPa·s, preferably at least 10 kPa·s, more preferably at least 11 kPa·s at 410° C. and a shear rate of 1 rad/sec, as measured using a parallel plates viscometer e.g. (TA ARES RDA3 model) in accordance with ASTM D4440. The (t-PAES) polymer of the present invention has a melt viscosity of advantageously of at most 149 kPa·s, preferably of at most 111 kPa·s, more preferably of at most 82 kPa·s at 410° C. and a shear rate of 1 rad/sec, as measured using a parallel plates viscometer (e.g. TA ARES RDA3 model) in accordance with ASTM D4440.

The (t-PAES) polymer of the present invention advantageously possesses a glass transition temperature of at least 210° C., preferably 220° C., more preferably at least 230° C.

Glass transition temperature (Tg) is generally determined by DSC, according to ASTM D3418.

The (t-PAES) polymer of the present invention advantageously possesses a melting temperature of at least 330° C., preferably 340° C., more preferably at least 350° C. The (t-PAES) polymer of the present invention advantageously possesses a melting temperature below 430° C., preferably below 420° C. and more preferably below 410° C.

The melting temperature (Tm) is generally determined by DSC, according to ASTM D3418.

It is known that the crystallinity of polymers is characterized by their degree of crystallinity and a semi-crystalline polymer having a higher number average molecular weight ($M_n$) is in general characterized by having a lower degree of crystallinity.

The Applicant has surprisingly found that the (t-PAES) polymers of the present invention having a number average molecular weight ($M_n$) ranging from 41 000 to 90 000 still maintain good crystallization properties.

The degree of crystallinity can be determined by different methods known in the art such as notably by Wide Angle X-Ray diffraction (WAXD) and Differential Scanning calorimetry (DSC).

For the purpose of the present invention, the degree of crystallinity has been measured by DSC on compression molded samples of the (t-PAES) polymers of the present invention, as described in detail in the experimental section.

According to the present invention, molded parts of the (t-PAES) polymer have advantageously a degree of crystallinity below 30%, preferably below 28% and more preferably below 26%.

According to the present invention, molded parts of the (t-PAES) polymer have advantageously a degree of crystallinity above 5%, preferably above 7% and more preferably above 8%.

Good results were obtained when molded parts of the (t-PAES) polymer had a degree of crystallinity from 9 to 25%.

The Applicant has found that the (t-PAES) polymers of the present invention has a solubility in an aqueous sulphuric acid solution having a density of 1.84 $g/cm^3$ advantageously of less than 10.0 g/l, preferably less than 1.00 g/l and more preferably less than 0.50 g/l.

As said, the (t-PAES) polymer of the present invention has been found to possess an excellent ductility, in other words, the (t-PAES) polymer of the present invention have high tensile yield elongation and tensile elongation at break values.

The (t-PAES) polymer of the present invention advantageously possesses a tensile yield elongation, as measured according to ASTM D638, equal to or above 2%, preferably equal to or above 3%, more preferably equal to or above 4%.

The (t-PAES) polymer of the present invention advantageously possesses a tensile yield elongation, as measured according to ASTM D638, equal to or below 25%, preferably equal to or below 20%, more preferably equal to or below 18%.

The (t-PAES) polymer of the present invention advantageously possesses a tensile elongation at break, as measured according to ASTM D638, equal to or above 9%, preferably equal to or above 10%, more preferably equal to or above 11%.

The (t-PAES) polymer of the present invention advantageously possesses a tensile elongation at break, as measured according to ASTM D638, equal to or below 40%, preferably equal to or below 35%, more preferably equal to or below 30%.

Manufacture of a (t-PAES) Polymer

To the aim to provide polyarylene ether sulfone (PAES) polymers comprising moieties derived from incorporation of 4,4"-terphenyl-p-diol wherein said (PAES) polymers have controlled high molecular weights, a new process for the manufacture of said (PAES) polymers has been developed thereby allowing an easy molecular weight control.

Thus, still another object of the present invention is a process for manufacturing a (t-PAES) polymer, wherein more than 70% moles of the recurring units are recurring units ($R_t$) of formula ($S_t$):

-E-Ar¹—SO₂—[Ar²-(T-Ar³)$_n$—SO₂]$_m$—Ar⁴—     (formula $S_t$)

wherein:
n and m, equal to or different from each other, are independently zero or an integer of 1 to 5,
each of Ar¹, Ar², Ar³ and Ar⁴ equal to or different from each other and at each occurrence, is an aromatic moiety,
T is a bond or a divalent group optionally comprising one or more than one heteroatom; preferably T is selected from the group consisting of a bond, —CH₂—, —C(O)—, —C(CH₃)₂—, —C(CF₃)₂—, —C(=CCl₂)—, —C(CH₃)(CH₂CH₂COOH)—, and a group of formula:

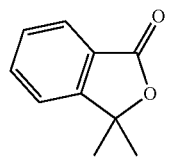

E is of formula ($E_t$):

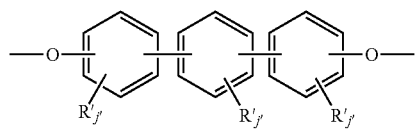

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 1 to 4, and wherein said (t-PAES) polymer is having a number average molecular weight ($M_n$) of at least 41 000.

Thus, the invention pertains to a process for the manufacturing of a (t-PAES) polymer, having a number average molecular weight ($M_n$) of at least 41 000, comprising reacting in a solvent mixture comprising a polar aprotic solvent and in the presence of an alkali metal carbonate, a monomer mixture which contains:
at least one dihydroxyaryl compound [diol (AA), hereinafter] of formula (T):

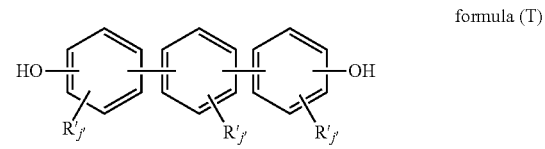

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 1 to 4
at least one dihaloaryl compound [dihalo(BB), hereinafter] of formula (S):

X—Ar¹—SO₂—[Ar²-(T-Ar³)$_n$—SO₂]$_m$—Ar⁴—X'     formula (S)

wherein
n and m, equal to or different from each other, are independently zero or an integer of 1 to 5; X and X', equal to or different from each other, are halogens selected from F, Cl, Br, I; preferably Cl or F.
each of Ar¹, Ar², Ar³ and Ar⁴ equal to or different from each other and at each occurrence, is an aromatic moiety.
T is a bond or a divalent group optionally comprising one or more than one heteroatom; preferably T is selected from the group consisting of a bond, —CH₂—, —C(O)—, —C(CH₃)₂—, —C(CF₃)₂—, —C(=CCl₂)—, —C(CH₃)(CH₂CH₂COOH)—, and a group of formula:

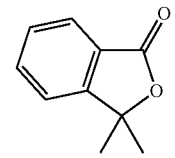

optionally, at least one dihydroxyaryl compound [diol (A'A')] different from diol (AA), as detailed above;

optionally, at least one dihaloaryl compound [dihalo (B'B')] different from dihalo (BB), as detailed above; being understood that the overall amount of halo-groups and hydroxyl-groups of the monomers of the monomer mixture is substantially equimolecular, so as to obtain a (t-PAES) polymer having a $M_n$ of at least 41 000, wherein the reaction is carried out at a total % monomer mixture concentration [total % monomers, herein after] equal to or more than 22% and less than 50% with respect to the combined weight of monomer mixture and solvent mixture.

For the purpose of the present invention, the term "total % monomers" is defined as the sum of the weight of all monomers initially present at the start of the reaction in the monomer mixture in grams, designated as $M_{wt}$, divided by the combined weight of all monomers initially present in the monomer mixture and of the solvent mixture, wherein the weight of the solvent mixture in grams is designated as $S_{wt}$.

The total % monomers is thus equal to the formula:

$$100 \times M_{wt}/(M_{wt}+S_{wt}).$$

The total % monomers is preferably equal to or more than 24%, more preferably equal to or more than 25%.

The total % monomers is in general less than 60%, preferably less than 50%, more preferably less than 45% and even more preferably less than 42%.

Very good results have been obtained at a total % monomers in a range from 25%-42%.

For the purpose of the present invention, the expression "substantially equimolecular" used with reference to the overall amount of halo-groups and hydroxyl-groups of the monomers initially present at the start of the reaction of the monomer mixture, as above detailed, is to be understood that the molar ratio of the overall amount of hydroxyl groups of the monomers of the monomer mixture to the overall amount of halo groups of the monomers of the monomer mixture is above 0.992, more preferably above 0.995. It is further understood that the molar ratio of the overall amount of hydroxyl groups of the monomers of the monomer mixture to the overall amount of halo groups of the monomers of the monomer mixture is below 1.01, preferably below 1.008, more preferably below 1.005. Good results were obtained when the molar ratio of the overall amount of hydroxyl groups of the monomers of the monomer mixture to the overall amount of halo groups of the monomers of the monomer mixture is about 1.00.

If desired, a small amount of the dihalo(BB), as described above, and/or dihalo (B'B'), as described above, can be added to the reaction mixture when the reaction is essentially complete.

For the purpose of the present invention, the expression "essentially complete" used with reference to the reaction is to be understood that the amount of all monomers which were initially present at the start of the reaction in the monomer mixture is below 1.5% mol, preferably below 1% mol, relative to the total amount of all monomers which were initially present at the start of the reaction.

Said small amount, expressed in a molar amount with respect to the total amount of moles of the diol (AA), as detailed above and optionally the diol (A'A'), as detailed above, is typically in the range from about 0.1 to 15% mol, with respect to the total amount of moles of the diol (AA), as detailed above, and optionally of the diol (A'A'), preferably from 0.2 to 10% mol, more preferably from 0.5 to 6% mol.

If desired, the solvent mixture can further comprise any end-capping agent [agent (E)]. Said agent (E) is in general selected from the group consisting of a halo compound comprising only one reactive halo group [agent (MX)] and a hydroxyl compound comprising only one reactive hydroxy group [agent (MOH)].

The expression 'halo compound comprising only one reactive halo group [agent (MX)]' is intended to encompass not only monohalogenated compounds but also halogenated compounds comprising more than one halo group, but wherein only one of said halo group is reactive.

It is nevertheless generally preferred that said agent (MX) comprises only one halo group.

Thus, agent (MX) is preferably selected from the group consisting of 4-monochlorodiphenylsulfone, 4-mono fluorodiphenylsulfone, 4-monofluorobenzophenone, 4-monochlorobenzophenone, alkylchlorides such as methylchloride and the like.

Similarly, the expression 'hydroxyl compound comprising only one reactive hydroxy group [agent (MOH)]' is intended to encompass not only monohydroxylated compounds but also hydroxylated compounds comprising more than one hydroxy group, but wherein only one of said hydroxy group is reactive.

It is nevertheless generally preferred that said agent (MOH) comprises only one hydroxy group.

Thus, agent (MOH) is preferably selected from the group consisting of terphenol, phenol, 4-phenylphenol, 4-phenoxyphenol, 4-monohydroxydiphenylsulfone, 4-monohydroxybenzophenone.

In the process of the present invention, the total amount of agent (E), computed as $$\text{agent}(E)(\% \text{ moles}) = \left[ \frac{\text{moles of agent } (MX)}{\text{total moles of } (dihalo(BB) + dihalo(B'B'))} + \frac{\text{moles of agent } (MOH)}{\text{total moles of } (diol\ (AA) + diol\ (A'A'))} \right] \cdot 100$$

is comprised between 0.05 and 20% moles, being understood that the agent (E) might advantageously be agent (MX) alone, agent (MOH) alone or a combination thereof. In other words, in above mentioned formula, the amount of agent (MX) with respect to the total moles of dihalo(BB), as detailed above, optionally of dihalo (B'B'), as detailed above, can be from 0.05 to 20% moles, the amount of agent (MOH) with respect to the total moles of diol (AA), as detailed above, and optionally of the diol (A'A'), can be from 0.05 to 20% moles, with the additional provisions that their sum is of 0.05 to 20% moles.

The amount of agent (E), as above described, is of at most 10% moles, preferably at most 8% moles, more preferably at most 6% moles.

The amount of agent (E), as above described, is of at least 1% moles, preferably at least 2% moles.

The agent (E) can be present at the start of the reaction in the monomer mixture or/and can be added to the reaction mixture when the reaction is essentially complete.

The agent (E) can be added with the aim to control the upper limit of the number average molecular weight ($M_n$) of the (t-PAES) polymer, as detailed above.

The aromatic moiety in each of $Ar^1$, $Ar^2$, $Ar^3$ and $Ar^4$ equal to or different from each other and at each occurrence is preferably complying with following formulae:

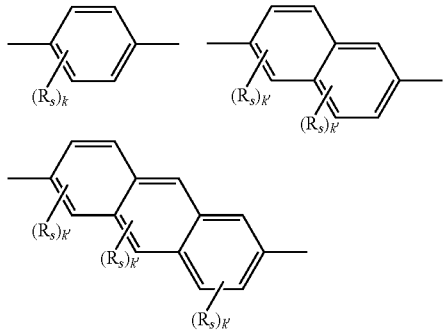

wherein:
each $R_s$ is independently selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and k is zero or an integer of 1 to 4; k' is zero or an integer of 1 to 3.

Preferred dihalo (BB) are those complying with formulae (S'-1) to (S'-4), as shown below:

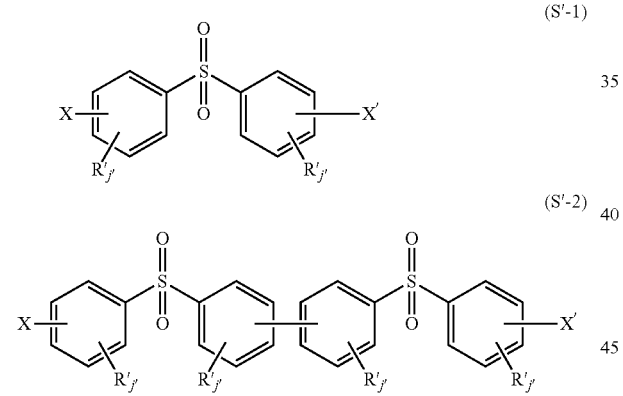

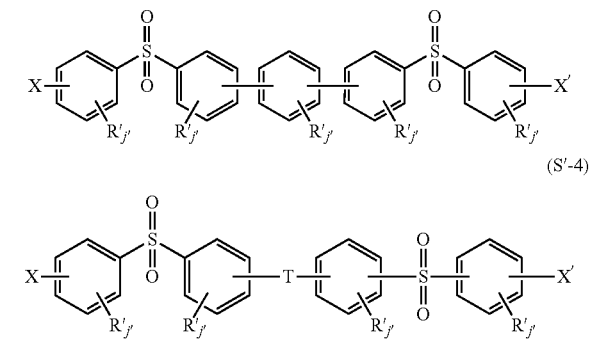

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

j' is zero or is an integer from 1 to 4,

T is a bond or a divalent group optionally comprising one or more than one heteroatom; preferably T is selected from the group consisting of a bond, —$CH_2$—, —C(O)—, —$C(CH_3)_2$—, —$C(CF_3)_2$—, —C(=$CCl_2$)—, —$C(CH_3)(CH_2CH_2COOH)$—, and a group of formula:

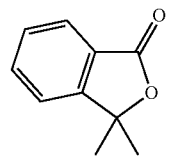

X and X', equal to or different from each other, are independently a halogen atom, preferably Cl or F.

More preferred dihalo (BB) are those complying with following formulae shown below:

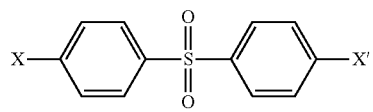

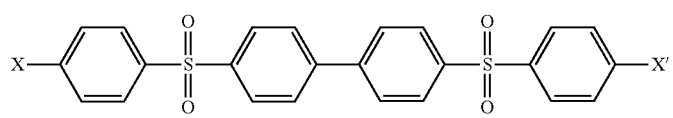

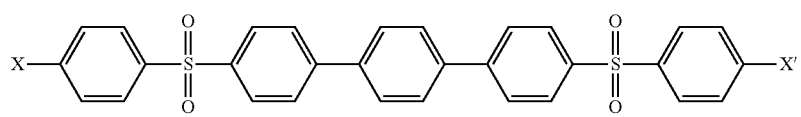

wherein X and X' are as defined above, X and X', equal to or different from each other, are preferably Cl or F. More preferably X and X' are F.

Preferred dihaloaryl compounds [dihalo (BB)] are 4,4'-difluorodiphenyl sulfone (DFDPS), 4,4'-dichlorodiphenyl sulfone (DCDPS), 4,4'-chlorofluorodiphenyl sulfone or a mixture thereof. Most preferred dihalo (BB) is 4,4'-difluorodiphenyl sulfone (DFDPS) or a mixture of DCDPS and DFDPS.

Among dihaloaryl compound [dihalo (B'B')] different from dihalo (BB) mention can be notably made of dihalo (B'B') of formula (K):

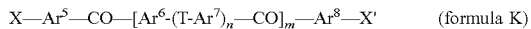

X—Ar$^5$—CO—[Ar$^6$-(T-Ar$^7$)$_n$—CO]$_m$—Ar$^8$—X'    (formula K)

wherein:
- n and m, equal to or different from each other, are independently zero or an integer of 1 to 5,
- each of Ar$^5$, Ar$^6$, Ar$^7$ and Ar$^8$ equal to or different from each other and at each occurrence, is an aromatic moiety,
- T is a bond or a divalent group optionally comprising one or more than one heteroatom; preferably T is selected from the group consisting of a bond, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

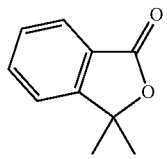

X and X', equal to or different from each other, are independently a halogen atom, preferably Cl or F.

More preferred dihalo (B'B') are those complying with following formulae shown below:

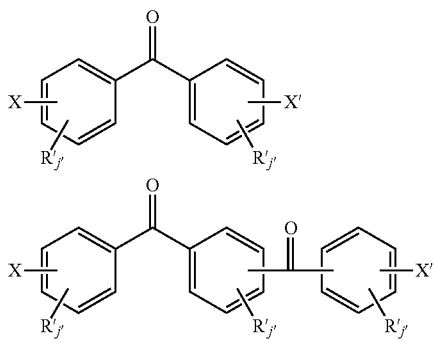

wherein
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
j' is zero or is an integer from 1 to 4;
wherein X and X' are as defined above, X and X', equal to or different from each other, are preferably Cl or F. More preferably X and X' are F.

Preferred dihalo (B'B') are 4,4'-difluorobenzophenone, 4,4'-dichlorobenzophenone and 4-chloro-4'-fluorobenzophenone, with 4,4'-difluorobenzophenone being particularly preferred.

Among dihydroxyl compounds [diols (A'A')] different from diol (AA), as above detailed, mention can be of compounds of formula (D):

HO—Ar$^9$-(T'-Ar$^{10}$)$_n$—O—H    formula (D)

wherein:
- n is zero or an integer of 1 to 5;
- each of Ar$^9$ and Ar$^{10}$, equal to or different from each other and at each occurrence, is an aromatic moiety of the formula:

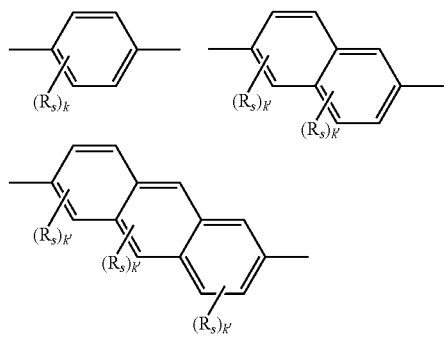

wherein:
each R$_s$ is independently selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and
k is zero or an integer of 1 to 4; k' is zero or an integer of 1 to 3;
T' is a bond or a divalent group optionally comprising one or more than one heteroatom; preferably T is selected from the group consisting of a bond, —SO$_2$—, —CH$_2$—, —C(O)—, —C(CH$_3$)$_2$—, —C(CF$_3$)$_2$—, —C(=CCl$_2$)—, —C(CH$_3$)(CH$_2$CH$_2$COOH)—, and a group of formula:

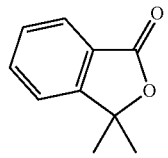

Among preferred dihydroxyl compounds [diols (A'A')] different from diol (AA), as above detailed, suitable for being used in the process of the present invention, mention may be notably made of the following molecules:

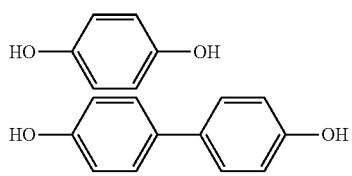

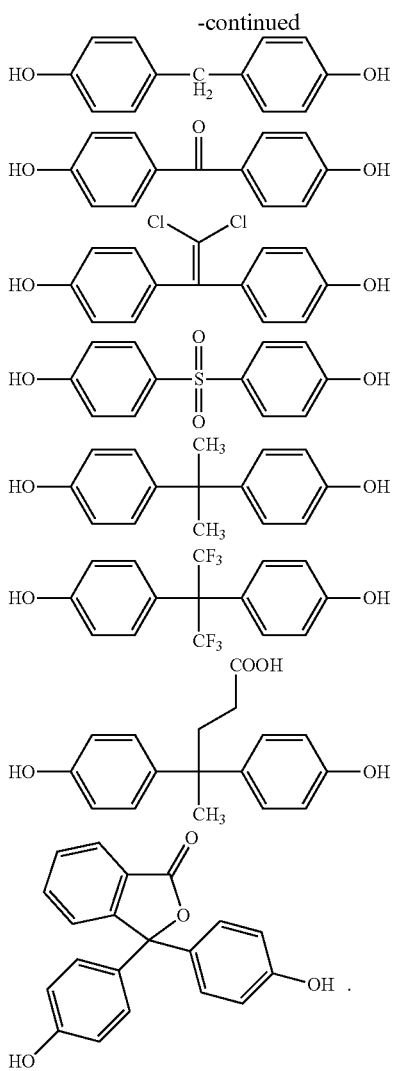

According to all embodiments of the present invention, the diol (AA) and dihalo (BB) and all other optional components (e.g. diol (A'A') and dihalo (B'B')) are dissolved or dispersed in a solvent mixture comprising a polar aprotic solvent.

As polar aprotic solvents, mention can be made of sulphur containing solvents such as notably aromatic sulfones and aromatic sulfoxides and more specifically diaromatic sulfones and diaromatic sulfoxides according to the general formulae below:

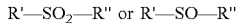

wherein R' and R", equal to or different from each other, are independently aryl, alkaryl and araryl groups.

More preferred polar aprotic solvents are those complying with following formulae shown below:

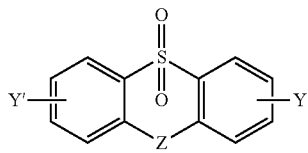

wherein Y and Y', equal to or different from each other, are independently selected from the group consisting of halogen, alkyl, alkenyl, alkynyl, aryl, alkaryl, aralkyl; Z is a bond, oxygen or two hydrogens (one attached to each benzene ring).

Specifically, among the sulphur-containing solvents that may be suitable for the purposes of this invention are diphenyl sulfone, phenyl tolyl sulfone, ditolyl sulfone, xylyl tolyl sulfone, dixylyl sulfone, tolyl paracymyl sulfone, phenyl biphenyl sulfone, tolyl biphenyl sulfone, xylyl biphenyl sulfone, phenyl naphthyl sulfone, tolyl naphthyl sulfone, xylyl naphthyl sulfone, diphenyl sulfoxide, phenyl tolyl sulfoxide, ditolyl sulfoxide, xylyl tolyl sulfoxide, dixylyl sulfoxide, dibenzothiophene dioxide, and mixtures thereof.

Very good results have been obtained with diphenyl sulfone.

Other carbonyl containing polar aprotic solvents, including benzophenone and the like have been disclosed in the art for use in these type of processes, and may also be found useful in the practice of this invention.

If desired, an additional solvent can be used together with the polar aprotic solvent which forms an azeotrope with water, whereby water formed as a by-product during the polymerization may be removed by continuous azeotropic distillation throughout the polymerization.

The by-product water and carbon dioxide possibly formed during the polymerization can alternatively be removed using a controlled stream of an inter gas such as nitrogen or argon over and/or in to the reaction mixture in addition to or advantageously in the absence of an azeotrope-forming solvent as described above.

For the purpose of the present invention, the term "additional solvent" is understood to denote a solvent different from the polar aprotic solvent and the reactants and the products of said reaction.

The additional solvent that forms an azeotrope with water will generally be selected to be inert with respect to the monomer components and polar aprotic solvent. Suitable azeotrope-forming solvents for use in such polymerization processes include aromatic hydrocarbons such as benzene, toluene, xylene, ethylbenzene, chlorobenzene and the like.

The azeotrope-forming solvent and polar aprotic solvent are typically employed in a weight ratio of from about 1:10 to about 1:1, preferably from about 1:5 to about 1:3.

The alkali metal carbonate is preferably sodium carbonate, potassium carbonate, rubidium carbonate and cesium carbonate. Sodium carbonate and especially potassium carbonate are preferred. Mixtures of more than one carbonates can be used, for example, a mixture of sodium carbonate or bicarbonate and a second alkali metal carbonate or bicarbonate having a higher atomic number than that of sodium.

The amount of said alkali metal carbonate used, when expressed by the ratio of the equivalents of alkali metal (M) per equivalent of hydroxyl group (OH) [eq. (M)/eq. (OH)] ranges from 1.00 to 1.50, preferably from 1.00 to 1.30, more preferably from about 1.00 to 1.20, most preferably from about 1.00 to 1.10 being understood that above mentioned hydroxyl group equivalents are comprehensive of those of the diol (AA), and, if present, of diol (A'A'). Very good results have been obtained with a ratio of eq. (M)/eq. (OH) of 1.01-1.10.

The Applicant has surprisingly found that the use of an optimum amount of alkali metal carbonate allows reducing significantly the reaction times of the process of the present invention while avoiding using excessive amounts of alkali metal carbonate which leads to higher costs and more difficult polymer purifications.

The use of an alkali metal carbonate having an average particle size of less than about 200 µm, preferably of less than about 150 µm preferably of less than about 75 µm, more preferably <45 µm is especially advantageous. The use of an alkali metal carbonate having such a particle size permits the synthesis of the polymers meeting our molecular weight requirements.

If desired, at least one salt (S1) able to react with a fluoride salt (S2) can be added to the reaction mixture. Said fluoride salt (S2) can be formed as one of the by-products during the polymerization reaction when X or/and X' in dihalo (BB) and/or dihalo (B'B') is F. Examples of such fluoride salt (S2) are notably sodium fluoride and potassium fluoride. Suitable salts (S1) for use in such polymerization processes include lithium chloride, calcium chloride and magnesium chloride. It is preferably lithium chloride.

The process according to the present invention is advantageously pursued while taking care to avoid the presence of any reactive gases in the reactor. These reactive gases may be notably oxygen, water and carbon dioxide. $O_2$ is the most reactive and should therefore be avoided.

In a particular embodiment, the reactor should be evacuated under pressure or under vacuum and filled with an inert gas containing less than 20 ppm of reactive gases, and in particular less than 10 ppm of $O_2$ prior to adding the alkali metal carbonate to the reaction mixture. Then, the reactor should be put under a constant purge of said inert gas until the end of the reaction. The inert gas is any gas that is not reactive under normal circumstances. It may be chosen from nitrogen, argon or helium. The inert gas contains preferably less than 10 ppm oxygen, 20 ppm water and 20 ppm carbon dioxide.

Generally, after an initial heat up period, the temperature of the reaction mixture will be maintained in a range of advantageously from 250 to 350° C., preferably from 300 to 340° C. Good results were obtained at a temperature at about 320° C.

In one embodiment of the process of the present invention, the alkali metal carbonate, in particular potassium carbonate is added to the monomer mixture at a temperature from 25 to 280° C., preferably from 120 to 270° C., more preferably from 180 to 250° C.

In a more preferred embodiment of the process of the invention, the alkali metal carbonate, in particular potassium carbonate is first added to the diol (AA), as described above, and optionally the diol (A'A'), as described above, in the solvent mixture, as described above, and the dihalo (BB), as detailed above and optionally the dihalo (B'B'), as detailed above, is then added to said reaction mixture at a temperature from 25 to 280° C., preferably from 120 to 270° C., more preferably from 180 to 250° C.

In general, the end-capping agent, as described above, is added to the reaction mixture, as described above, at a temperature from 250 to 350° C., preferably from 300 to 340° C.

The (t-PAES) polymer of the present invention, can notably be used in HP/HT applications.

As per the processing, the (t-PAES) polymer of the present invention, can be advantageously processed for yielding articles by melt processing (including injection moulding, extrusion moulding, compression moulding), but also by other processing procedures such as notably spray coating, powder coating selective sintering, fused deposition modelling and the like.

It is another object of the present invention to provide a shaped article comprising the (t-PAES) polymer of the present invention.

Should the disclosure of any patents, patent applications, and publications which are incorporated herein by reference conflict with the description of the present application to the extent that it may render a term unclear, the present description shall take precedence.

The invention will be now described in more details with reference to the following examples, whose purpose is merely illustrative and not intended to limit the scope of the invention.

Raw Materials 1,1':4',1''-terphenyl-4,4''-diol commercially available from Yonghi Chemicals, China, further purified by washing with ethanol/water (90/10) at reflux. The purity of the resulting material was shown to be higher than 94.0% area as measured by Gas Chromatography.

4,4'-difluorodiphenylsulfone commercially available from Aldrich (99% grade, 99.32% measured) or from Marshallton (99.92% pure by GC).

Diphenyl sulfone (polymer grade) commercially available from Proviron (99.8% pure).

Potassium carbonate with a $d_{90}$<45 µm commercially available from Armand products.

Lithium chloride (99+%, ACS grade) commercially available from Acros.

General Description of the Preparation of the (t-PAES) Polymer

In a 500 mL 4-neck reaction flask fitted with a stirrer, a $N_2$ inlet tube, a Claisen adapter with a thermocouple plunging in the reaction medium, and a Dean-Stark trap with a condenser and a dry ice trap were introduced 89.25 g of diphenyl sulfone, 28.853 g of 1,1':4',1''-terphenyl-4,4''-diol and 27.968 g of 4,4'-difluorodiphenylsulfone, corresponding to a total % monomers of 38.9% and molar ratio dihalo (BB)/diol of 1.000. The flask content was evacuated under vacuum and then filled with high purity nitrogen (containing less than 10 ppm $O_2$). The reaction mixture was then placed under a constant nitrogen purge (60 mL/min). The reaction mixture was heated slowly to 220° C. At 220° C., 15.354 g of $K_2CO_3$ were added via a powder dispenser to the reaction mixture over 30 minutes. At the end of the addition, the reaction mixture was heated to 320° C. at 1° C./minute. After the appropriate reaction time, expressed in minutes in Table 1 below, at 320° C., 1.119 g of 4,4'-difluorodiphenylsulfone were added to the reaction mixture while keeping a nitrogen purge on the reactor. After 2 minutes, 4.663 g of lithium chloride were added to the reaction mixture. 2 minutes later, another 0.280 g of 4,4'-difluorodiphenylsulfone were added to the reactor and the reaction mixture was kept at temperature for 5 minutes. The reactor content was then poured from the reactor into a stainless steel pan and cooled. The solid was broken up and ground in an attrition mill through a 2 mm screen. Diphenyl sulfone and salts were extracted from the mixture with acetone then water at pH between 12 and 11 then with acetone. The powder was then washed with 1200 mL water containing 2 g of sodium dihydrogen phosphate and 2 g of sodium monohydrogenphosphate. The powder was then removed from the reactor and dried at 120° C. under vacuum for 12 hours yielding 44 g of a light brown powder. The molecular weight of the final polymer was measured by the GPC developed, as detailed below. The reaction times at 320° C. and all results are summarized in Table 2.

Comparative Example 1

Said comparative example was performed following the synthesis procedure as 2 described in EP 0 383 600 A2 under heading Example 1, which is incorporated herein in its entirety by reference, but by using 100.00 g of diphenyl sulphone, 13.115 g of 1,1':4',1"-terphenyl-4,4"-diol and 12.840 g of 4,4'-difluorodiphenylsulfone. The total % monomers is 20.6% and molar ratio dihalo (BB)/diol is 1.020. All results are summarized in Table 2.

Comparative Example 1'

Said comparative example was performed following the synthesis procedure as described in GB 2 289 685 A under heading Example 12, which is incorporated herein in its entirety by reference, but by using 100.00 g of diphenyl sulphone, 20.997 g of 1,1':4',1"-terphenyl-4,4"-diol and 20.524 g of 4,4'-difluorodiphenylsulfone. The total % monomers is 29.4.6% and molar ratio dihalo (BB)/diol is 1.0084. All results are summarized in Table 2.

Comparative Examples 2-4 and Examples 5-10

All these examples were carried out according to the general procedure and the corresponding reaction times at 320° C. are shown in Table 2.

Example 11

This example was carried out according to the general procedure except that in the 500 mL 4-neck reaction flask fitted with a stirrer, a $N_2$ inlet tube, a Claisen adapter with a thermocouple plunging in the reaction medium, and a Dean-Stark trap with a condenser and a dry ice trap were introduced 89.26 g of diphenyl sulfone, 28.853 g of 1,1':4',1"-terphenyl-4,4"-diol and 15.354 g of $K_2CO_3$, and after the reaction mixture was heated slowly to 220° C., 28.0514 g of 4,4'-difluorodiphenylsulfone were added via a powder dispenser to the reaction mixture over 20 minutes. At the end of the addition, the reaction mixture was heated to 320° C. at 1° C./minute. After 10 minutes at 320° C., 0.5594 g of 4,4'-difluorodiphenylsulfone were added to the reaction mixture while keeping a nitrogen purge on the reactor. After removal of diphenyl sulfone and salts, 48 g of a light brown powder was obtained. The molecular weight of the final polymer was measured by the GPC developed as detailed below. The reaction times at 320° C. and all results are summarized in Table 2.

Comparative Examples C12-C14 and 15-17 and 19

All these examples are carried out according to the general procedure and the corresponding reaction conditions are shown in Table 3.

Example 18

The example was carried out according to the general procedure of example 11, except that 89.25 g of diphenyl sulfone, 28.853 g of 1,1':4',1"-terphenyl-4,4"-diol and 28.163 g of 4,4'-difluorodiphenylsulfone were used. The total % monomers is 39.0% and molar ratio dihalo (BB)/diol is 1.007. All results are summarized in Table 3.

The following characterizations carried out on the materials of the Examples are indicated hereinafter:
Molecular Weight Measurements by a GPC Method
GPC Condition:
Pump: 515 HPLC pump manufactured by Waters
Detector: UV 1050 series manufactured by HP
Software: Empower Pro manufactured by Waters
Injector: Waters 717 Plus Auto sampler
Flow rate: 0.5 ml/min
UV detection: 270 nm
Column temperature: 40° C.
Column: 2×PL Gel mixed D, 5 micron, 300 mm×7.5 mm 5 micron manufactured by Agilent
Injection: 20μ liter
Runtime: 60 minutes
Eluent: N-Methyl-2-pyrrolidone (Sigma-Aldrich, Chromasolv Plus for HPLC>99%) with 0.1 mol Lithium bromide (Fisher make). Mobile phase should be store under nitrogen or inert environment
Calibration standard: Polystyrene standards part number PL2010-0300 manufactured by Agilent was used for calibration. Each vial contains a mixture of four narrow polydispersity polystyrene standards (a total 11 standard, 371100, 238700, 91800, 46500, 24600, 10110, 4910, 2590, 1570, 780 used to establish calibration curve).
Concentration of standard: 1 milliliter of mobile phase added in to each vial before GPC injection for calibration.
Calibration Curve: 1) Type: Relative, Narrow Standard Calibration 2) Fit: $3^{rd}$ order regression.
Integration and calculation: Empower Pro GPC software manufactured by Waters used to acquire data, calibration and molecular weight calculation. Peak integration start and end points are manually determined from significant difference on global baseline.
Sample Preparation:
25 mg of the (t-PAES) polymer was dissolved in 10 ml of 4-chlorophenol upon heating at 170 to 200° C. A small amount (0.2 to 0.4 ml) of said solution obtained was diluted with 4 ml of N-Methyl-2-pyrrolidone. The resulting solution was passed through to GPC column according to the GPC conditions mentioned above.
Viscosity Measurements
The melt viscosity was measured on a compression molded disk (25 mm in diameter by 3 mm thickness) with a TA ARES RDA3 Rheometer according to ASTM D4440 using the following conditions:
under nitrogen
410° C.
1 to 100 rad/sec frequency sweep
5% strain
Physical Property Measurements
DSC measurements were done according to ASTM D3418-03, E1356-03, E793-06, E794-06 on TA Instruments Q20 with nitrogen as carrier gas (99.998% purity, 50 mL/min). Temperature and heat flow calibrations were done using indium. Sample size was 5 to 7 mg. The weight was recorded ±0.01 mg.
The heat cycles were:
$1^{st}$ heat cycle: 50.00° C. to 450.00° C. at 20.00° C./min, isothermal at 450.00° C. for 1 min.
$1^{st}$ cool cycle: 450.00° C. to 50.00° C. at 20.00° C./min, isothermal for 1 min.
$2^{nd}$ heat cycle: 50.00° C. to 450.00° C. at 20.00° C./min, isothermal at 380.00° C. for 1 min.
The melting temperature (Tm melting point) was measured on the polymer powder according to the ASTM D3418: the temperature at which the main melting endotherm is observed in the $1^{st}$ heat cycle (20° C./min) is the Tm.
The glass transition temperature was measured from the $2^{nd}$ heat thermogram according to the ASTM D3418, by drawing a baseline before the transition and a baseline after the transition: the Tg is the temperature at half height between these two lines.

Crystallinity Measurements:

A 102 mm×102 mm×1.6 mm plaque was prepared from the (t-PAES) polymers by compression molding under the following conditions as shown in Table 1 below:

TABLE 1

| Step # | |
|---|---|
| 1 | preheat at 420° C. |
| 2 | 420° C./15 minutes, 2000 kg-f |
| 3 | 420° C./2 minutes, 2700 kg-f |
| 4 | cool down to 320° C. over 20 minutes, 2000 kg-f |
| 5 | 90 minute-hold at 320° C., 2000 kg-f |
| 6 | 25 minute-cool down to 30° C., 2000 kg-f |

The plaque was then annealed at 350° C. for 3 hours under air.

The % crystallinity of molded plaques was determined by measuring the enthalpy of fusion on the first heat scan. The melting of the part was taken as the area over a linear baseline drawn from 320° C. to a temperature above the last endotherm (typically 420° C.). The crystallinity level of the annealed plaque was determined by comparing the measured melting endotherm to the one of a 100% crystalline material (assumed to be 130 J/g).

Mechanical Properties

The mechanical properties of the (t-PAES) polymers were tested according to ASTM D638 using a Type L impact bars (ASTM D1822, 1/8"×3/8") as test specimen which were prepared from the annealed plaque, as mentioned above. The tensile properties were measured at 0.05 inch/minute.

The mechanical properties are summarized in Table 2.

TABLE 2

| Examples | C1[a] | C1'[e] | C2 | C3 | C4 | 5 | 6 |
|---|---|---|---|---|---|---|---|
| Reaction time at 320° C. (min) | 120 (at 300° C.) | 150 (at 300° C.) | 6 | 13 | 7 | 19 | 77 |
| Molecular weight data | | | | | | | |
| $M_n$ | 13701 | 40117 | 37119 | 37482 | 40248 | 41841 | 43170 |
| $M_w$ | 29993 | 109041 | 73416 | 74118 | 83646 | 82519 | 130648 |
| $M_z$ | 66350 | 242829 | 126645 | 129256 | 144466 | 139737 | 398606 |
| $M_w/M_n$ | 2.19 | 2.72 | 1.98 | 1.98 | 2.08 | 1.97 | 3.03 |
| $M_z/M_w$ | 2.21 | 2.23 | 1.73 | 1.74 | 1.73 | 1.69 | 3.05 |
| RV (dL/g) | not dissolved [c] | | | | | | |
| $MV^d$ (10 rad/sec) (Pa*s) | | | | | | 3290 | |
| $MV^d$ (1 rad/sec) (Pa*s) | | | | | | 10734 | |
| Physical properties | | | | | | | |
| Tg (° C.) | 232 | 252 | 250 | 226 | 249 | 254 | 251 |
| Tm (° C.) | 348 | 379 | 380 | 372 | 379 | 377 | 370 |
| Crystallinity level (%) | 38[b] | | 30 | 31 | 32 | 24 | 25 |
| Mechanical properties | | | | | | | |
| Tensile Strength at yield (psi) | N/A | N/A[f] | N/A | N/A | N/A | 11600 | 11100 |
| Tensile Yield Elongation (%) | N/A | 0[f] | — | — | — | 9.6 | 8.8 |
| Tensile Strength at break (psi) | N/A | N/A | 12400 | 11300 | 11000 | 9910 | 9940 |
| Tensile Elongation at Break (%) | N/A | 0[f] | 8.0 | 6.4 | 8.7 | 12.0 | 22.0 |
| Young Modulus (Kpsi) | N/A | N/A | 345 | 337 | 294 | 322 | 290 |

| Examples | 7 | 8 | 9 | 10 | 11 |
|---|---|---|---|---|---|
| Reaction time at 320° C. (min) | 13 | 90 | 32 | 62 | 10 |
| Molecular weight data | | | | | |
| $M_n$ | 43739 | 44407 | 48077 | 48621 | 78723 |
| $M_w$ | 87813 | 112679 | 96879 | 136747 | 165399 |
| $M_z$ | 149947 | 341156 | 163692 | 409845 | 308848 |
| $M_w/M_n$ | 2.01 | 2.54 | 2.02 | 2.81 | 2.10 |
| $M_z/M_w$ | 1.71 | 3.03 | 1.69 | 3.00 | 1.87 |
| RV (dL/g) | | Insoluble [c] | | | |
| $MV^d$ (10 rad/sec) (Pa*s) | 3790 | 7350 | | | |
| $MV^d$ (1 rad/sec) (Pa*s) | 14120 | 23940 | | | |
| Physical properties | | | | | |
| Tg (° C.) | 251 | 253 | 255 | 253 | 257 |
| Tm (° C.) | 377 | 373 | 376 | 370 | 386 |
| Crystallinity level (%) | 21 | 23 | 22 | 22 | 9 |

TABLE 2-continued

| Mechanical properties | | | | | |
|---|---|---|---|---|---|
| Tensile Strength at yield (psi) | 11100 | 11400 | 10700 | 10700 | 10854 |
| Tensile Yield Elongation (%) | 9.8 | 9.1 | 9.8 | 9.1 | 9.1 |
| Tensile Strength at break (psi) | 9610 | 9710 | 9500 | 9620 | 8832 |
| Tensile Elongation at Break (%) | 15.0 | 22.0 | 15.0 | 25.0 | 25.0 |
| Young Modulus (Kpsi) | 301 | 287 | 306 | 272 | 344 |

[a] C1 has been prepared following the synthesis procedure corresponding to example 2 as described in EP 0 383 600 A2

[b] Crystallinity on the molded annealed polymer at 325° C. as disclosed in Bulletin des Sociétés Chimiques Belges, 1989, 98 (9-10), pages 667-676.

[c] The sample obtained, did not dissolve in $H_2SO_4$ even after 6 months thus RV could not be measured.

[d] Viscosity measurements were carried out according to ASTM D4440

[e] C1' has been prepared following the synthesis procedure corresponding to example 12 as described in GB 2 289 685 A

[f] The plaque could not be taken out of the mold without breaking, hence, the product is brittle and does not yield

TABLE 3

| Examples No | C12 | C13 | C14 | 15 | 16 | 17 | 18 | 19 |
|---|---|---|---|---|---|---|---|---|
| dihalo (BB) → | | | | DFDPS | | | | |
| Reaction parameters: | | | | | | | Reverse add | |
| Weight of DPS (g) | 121.00 | 121.00 | 121.00 | 121.00 | 121.70 | 204.50 | 89.25 | 204.50 |
| Weight 1,1':4',1''-terphenyl-4,4''-diol (g) | 22.5185 | 22.5185 | 22.5185 | 22.2955 | 39.3450 | 66.4301 | 28.8530 | 66.0996 |
| Weight dihalo (BB) | 21.6113 | 21.6113 | 21.6113 | 21.6113 | 38.1375 | 64.0710 | 28.1633 | 64.0710 |
| Molar Ratio dihalo (BB)/diol | 0.990 | 0.990 | 0.990 | 1.000 | 1.000 | 0.995 | 1.007 | 1.000 |
| Molar Ratio $K_2CO_3$/diol | 1.00 | 1.02 | 1.02 | 1.03 | 1.01 | 1.01 | 1.01 | 1.025 |
| Sum of the weight of all monomers (g) | | | | | | | | |
| Total % monomers | 26.7 | 26.7 | 26.7 | 26.6 | 38.9 | 39.0 | 39.0 | 38.9 |
| Reaction time (min) | 75 | 10 | 36 | 15 | 27 | 63 | 2 | 38 |
| Polymer properties | | | | | | | | |
| $M_n$ | 22284 | 40149 | 34131 | 56058 | 48778 | 43614 | 42724 | 43683 |
| $M_w$ | 44409 | 79784 | 70259 | 115557 | 100144 | 108886 | 114982 | 118656 |
| $M_z$ | 80420 | 130999 | 120189 | 181896 | 163501 | 299033 | 411873 | 424585 |
| $M_w/M_n$ | 1.99 | 1.99 | 2.06 | 2.06 | 2.05 | 2.50 | 2.69 | 2.72 |
| $M_z/M_w$ | 1.81 | 1.64 | 1.71 | 1.57 | 1.63 | 2.75 | 3.58 | 3.58 |

The invention claimed is:

1. A poly(arylether sulfone) polymer, (t-PAES) polymer, wherein more than 70% moles of the recurring units are recurring units ($R_t$) of formula ($S_t$):

-E-Ar$^1$—SO$_2$—[Ar$^2$-(T-Ar$^3$)$_n$—SO$_2$]$_m$—Ar$^4$—   (formula $S_t$)

wherein:

n and m, equal to or different from each other, are independently zero or an integer of 1 to 5;

each of Ar$^1$, Ar$^2$, Ar$^3$ and Ar$^4$ equal to or different from each other and at each occurrence, is an aromatic moiety;

T is a bond or a divalent group optionally comprising one or more than one heteroatom;

E is of formula ($E_t$):

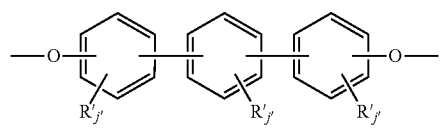

wherein:

each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

j' is zero or is an integer from 1 to 4; and said (t-PAES) polymer having a number average molecular weight ($M_n$) ranging from 41,000 to 90,000 and a polydispersity index of less than 4.0.

2. The (t-PAES) polymer of claim 1, wherein said (t-PAES) polymer has a solubility in an aqueous sulphuric acid solution having a density of 1.84 g/cm$^3$ of less than 1.00 g/l.

3. The (t-PAES) polymer according to claim 1, wherein said recurring units ($R_t$) are selected from the group consisting of formula ($S_t$-1) to ($S_t$-4):

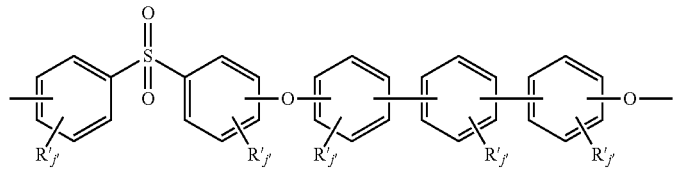

(S<sub>r</sub>-1)

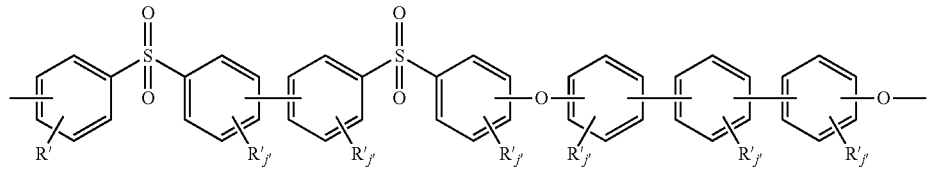

(S<sub>r</sub>-2)

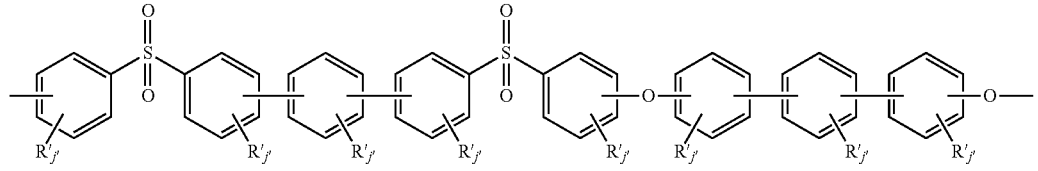

(S<sub>r</sub>-3)

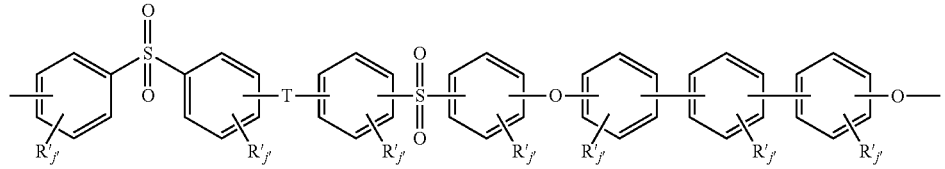

(S<sub>r</sub>-4)

wherein
- each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;
- j' is zero or is an integer from 1 to 4; and
- T is a bond or a divalent group optionally comprising one or more than one heteroatom.

4. The (t-PAES) polymer according to claim 1, additionally comprising recurring units ($R_a$) of formula ($K_a$):

wherein:
- n and m, equal to or different from each other, are independently zero or an integer of 1 to 5;
- each of $Ar^5$, $Ar^6$, $Ar^7$ and $Ar^8$ equal to or different from each other and at each occurrence, is an aromatic moiety;
- T is a bond or a divalent group optionally comprising one or more than one heteroatom;
- E is of formula ($E_t$):

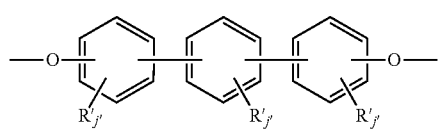

wherein:
- each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium.

5. The (t-PAES) polymer according to claim 1, additionally comprising recurring units ($R_b$) comprising a Ar—$SO_2$—Ar' group, with Ar and Ar', equal to or different from each other, being aromatic groups, said recurring units ($R_b$) complying with formulae (S1):

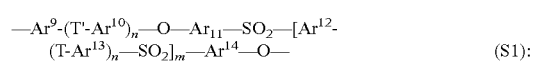

wherein:
- $Ar^9$, $Ar^{10}$, $Ar^{11}$, $Ar^{12}$, $Ar^{13}$ and $Ar^{14}$, equal to or different from each other and at each occurrence, are independently an aromatic mono- or polynuclear group;
- T and T', equal to or different from each other and at each occurrence, is independently a bond or a divalent group optionally comprising one or more than one heteroatom; and
- n and m, equal to or different from each other, are independently zero or an integer of 1 to 5.

6. The (t-PAES) polymer according to claim 1, additionally comprising recurring units ($R_c$) comprising a Ar—C(O)—Ar' group, with Ar and Ar', equal to or different from each other, being aromatic groups, said recurring units ($R_c$) are selected from the group consisting of formulae (J-A) to (J-L):

(J-A)
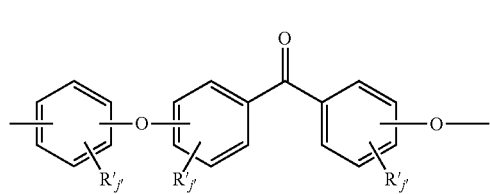
(J-B)
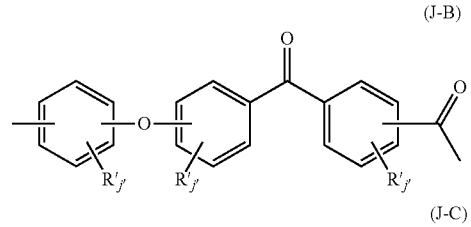
(J-C)
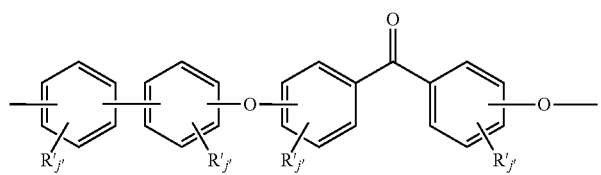
(J-D)
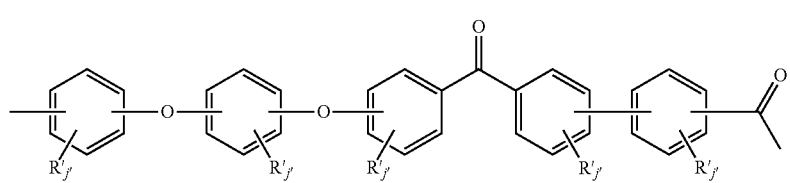
(J-E)
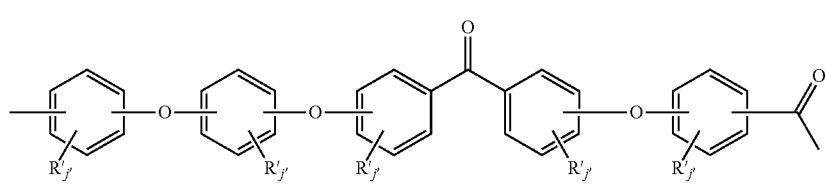
(J-F)
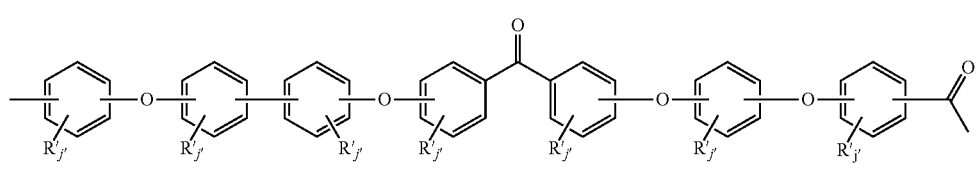
(J-G)
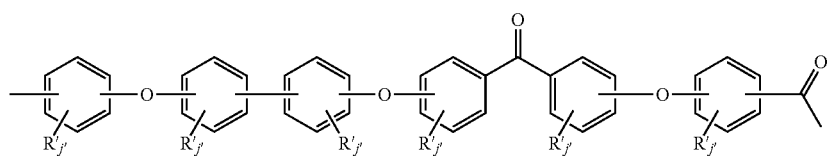
(J-H)
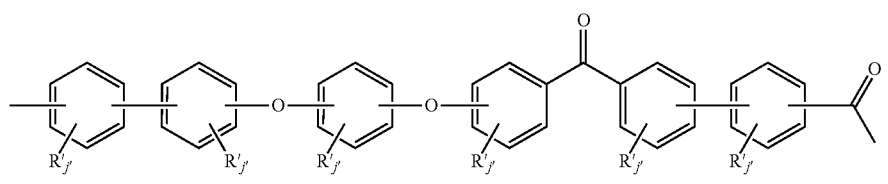
(J-I)
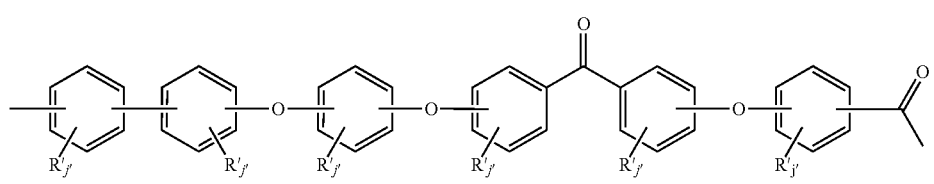
(J-J)
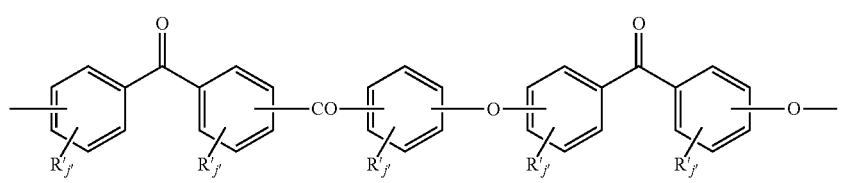

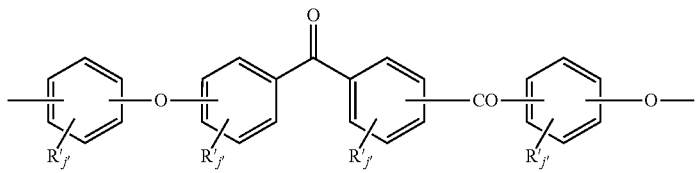

(J-K)

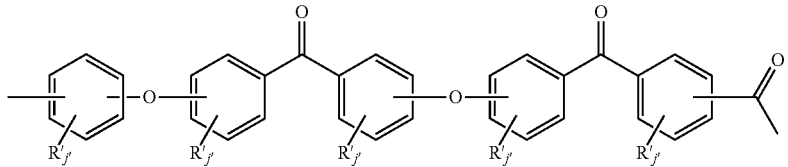

(J-L)

wherein:
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and j' is zero or is an integer from 0 to 4.

7. The (t-PAES) polymer according to claim 1, wherein the (t-PAES) polymer has a tensile yield elongation, as measured according to ASTM D638, equal to or above 2%.

8. The (t-PAES) polymer according to claim 1, wherein the (t-PAES) polymer has a tensile elongation at break, as measured according to ASTM D638, equal to or above 9%.

9. The (t-PAES) polymer of claim 1, wherein molded parts of the (t-PAES) polymer have a degree of crystallinity below 30% and wherein said molded parts are 102 mm×102 mm×1.6 mm plaques made by compression molding of said (t-PAES) polymer and wherein said plaques were annealed at 350° C. for 3 hours under air.

10. A gel-permeation chromatography (GPC) method for determining the number average molecular weight ($M_n$) of a poly(arylether sulfone) polymer, (t-PAES) polymer, wherein more than 70% moles of the recurring units are recurring units ($R_t$) of formula ($S_t$):

-E-Ar$^1$—SO$_2$—[Ar$^2$-(T-Ar$^3$)$_n$—SO$_2$]$_m$—Ar$^4$—  (formula $S_t$)

wherein:
n and m, equal to or different from each other, are independently zero or an integer of 1 to 5;
each of Ar$^1$, Ar$^2$, Ar$^3$ and Ar$^4$ equal to or different from each other and at each occurrence, is an aromatic moiety;
T is a bond or a divalent group optionally comprising one or more than one heteroatom;
E is of formula ($E_t$):

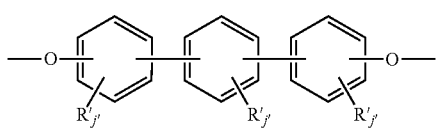

wherein:
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

j' is zero or is an integer from 1 to 4, said (t-PAES) polymer having a number average molecular weight ($M_n$) ranging from 41,000 to 90,000 and a polydispersity index of less than 4.0, wherein said GPC method comprises (i) dissolving said (t-PAES) polymer at a temperature from 100 to 250° C. in a solvent suitable for GPC providing a polymer solution wherein the concentration of said (t-PAES) polymer in said polymer solution is between 1.0 to 10.0 mg/ml, and (ii) eluting a specimen of said polymer solution in a GPC column using N-methyl-2-pyrrolidone (NMP) containing at least one salt as eluent, at a temperature from 20 to 50° C.

11. A process for manufacturing the (t-PAES) polymer according to claim 1, having a number average molecular weight ($M_n$) of at ranging from 41,000 to 90,000 and a polydispersity index of less than 4.0, comprising reacting in a solvent mixture comprising a polar aprotic solvent and in the presence of an alkali metal carbonate, a monomer mixture comprising:
at least one dihydroxyaryl compound, diol (AA), of formula (T):

formula (T)

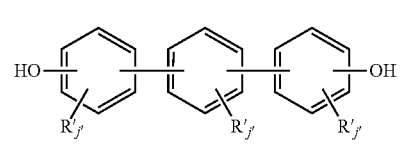

wherein:
each of R', equal to or different from each other, is selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium;

j' is zero or is an integer from 1 to 4;
at least one dihaloaryl compound, dihalo(BB), of formula (S):

X—Ar$^1$—SO$_2$—[Ar$^2$-(T-Ar$^3$)$_n$—SO$_2$]$_m$—Ar$^4$—X'  formula (S)

wherein:
n and m, equal to or different from each other, are independently zero or an integer of 1 to 5; X and X', equal to or different from each other, are halogens selected from F, Cl, Br, I;
each of $Ar^1$, $Ar^2$, $Ar^3$ and $Ar^4$ equal to or different from each other and at each occurrence, is an aromatic moiety;
T is a bond or a divalent group optionally comprising one or more than one heteroatom;
optionally, at least one dihydroxyaryl compound, diol (A'A'), different from diol (AA);
optionally, at least one dihaloaryl compound, dihalo (B'B'), different from dihalo (BB);
wherein the overall amount of halo-groups and hydroxyl-groups of the monomers of the monomer mixture is substantially equimolecular, wherein the reaction is carried out at a total % monomer mixture concentration, total % monomers, equal to or more than 22% and less than 50% with respect to the combined weight of monomer mixture and solvent mixture.

12. The process according to claim 11, wherein the monomer mixture comprises at least one dihaloaryl compound, dihalo (B'B'), different from dihalo (BB) of formula (K):

$$X-Ar^5-CO-[Ar^6-(T-Ar^7)_n-CO]_m-Ar^8-X' \quad \text{(formula K)}$$

wherein:
n and m, equal to or different from each other, are independently zero or an integer of 1 to 5;
each of $Ar^5$, $Ar^6$, $Ar^7$ and $Ar^8$ equal to or different from each other and at each occurrence, is an aromatic moiety;
T is a bond or a divalent group optionally comprising one or more than one heteroatom; and
X and X', equal to or different from each other, are independently a halogen atom.

13. The process according to claim 11, wherein the monomer mixture comprises at least one dihydroxyl compounds diol (A'A') different from diol (AA), selected from the group consisting of compounds of formula (D):

$$HO-Ar^9-(T'-Ar^{10})_n-O-H \quad \text{formula (D)}$$

wherein:
n is zero or an integer of 1 to 5;
each of $Ar^9$ and $Ar^{10}$, equal to or different from each other and at each occurrence, is an aromatic moiety of the formula:

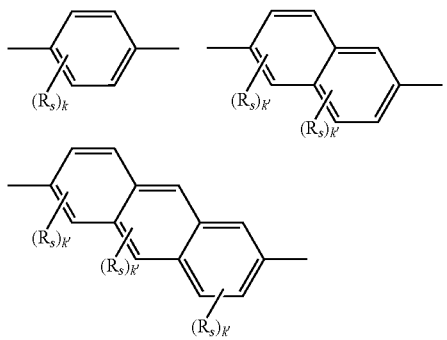

wherein:
each $R_s$ is independently selected from the group consisting of halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium; and
k is zero or an integer of 1 to 4; k' is zero or an integer of 1 to 3; and
T' is a bond or a divalent group optionally comprising one or more than one heteroatom.

14. A method for manufacturing shaped articles comprising processing the (t-PAES) polymer according to claim 1.

15. The method according to claim 14, wherein said (t-PAES) polymer is processed by melt processing; processing procedures selected from the group consisting of spray coating, powder coating selective sintering, fused deposition modelling; and combinations thereof.

16. A shaped article manufactured from the (t-PAES) polymer according to claim 1.

17. The (t-PAES) polymer of claim 1, wherein T is selected from the group consisting of a bond, —$CH_2$—, —C(O)—, —C($CH_3$)$_2$—, —C($CF_3$)$_2$—, —C(=$CCl_2$)—, —C($CH_3$)($CH_2CH_2COOH$)—, and a group of formula:

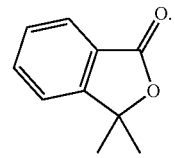

18. The (t-PAES) polymer of claim 5, wherein T' is selected from the group consisting of a bond, —$CH_2$—, —C(O)—, —C($CH_3$)$_2$—, —C($CF_3$)$_2$—, —C(=$CCl_2$)—, —C($CH_3$)($CH_2CH_2COOH$)—, —$SO_2$—, and a group of formula:

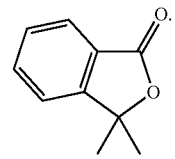

19. The (t-PAES) polymer according to claim 1, wherein the (t-PAES) polymer has a polydispersity index of less than 3.8.

20. The (t-PAES) polymer according to claim 1, wherein the (t-PAES) polymer has a polydispersity index of less than 3.5.

21. The method according to claim 15, wherein the melt processing is selected from injection moulding, extrusion moulding, compression moulding, and combinations thereof.

* * * * *